United States Patent
Hull et al.

(10) Patent No.: US 10,379,068 B2
(45) Date of Patent: Aug. 13, 2019

(54) NANO-LEVEL EVALUATION OF KEROGEN-RICH RESERVOIR ROCK

(71) Applicant: Saudi Arabian Oil Company, Dhahran (SA)

(72) Inventors: Katherine Leigh Hull, Houston, TX (US); Younane N. Abousleiman, Norman, OK (US)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 16/122,701

(22) Filed: Sep. 5, 2018

(65) Prior Publication Data

US 2019/0003992 A1 Jan. 3, 2019

(51) Int. Cl.

| | |
|---|---|
| *G01V 5/00* | (2006.01) |
| *G01N 23/20025* | (2018.01) |
| *G01N 3/08* | (2006.01) |
| *G01N 33/24* | (2006.01) |
| *G01N 23/20091* | (2018.01) |
| *E21B 49/00* | (2006.01) |
| *G01N 23/02* | (2006.01) |
| *G01N 3/06* | (2006.01) |

(52) U.S. Cl.
CPC ....... *G01N 23/20025* (2013.01); *E21B 49/00* (2013.01); *G01N 3/068* (2013.01); *G01N 3/08* (2013.01); *G01N 23/02* (2013.01); *G01N 23/20091* (2013.01); *G01N 33/24* (2013.01); *G01V 5/00* (2013.01); *G01N 2203/0286* (2013.01); *G01N 2203/0647* (2013.01); *G01N 2223/102* (2013.01); *G01N 2223/616* (2013.01)

(58) Field of Classification Search
CPC .... G01N 23/20025; G01N 3/068; G01N 3/08; G01N 23/02; G01N 23/20091; G01N 33/24; G01N 2203/0286; G01N 2203/0647; G01N 2223/102; G01N 2223/616; G01V 5/00
See application file for complete search history.

(56) References Cited

U.S. PATENT DOCUMENTS

| | | | |
|---|---|---|---|
| 4,220,550 | A | 9/1980 | Frenier et al. |
| 4,289,639 | A | 9/1981 | Buske |
| 4,381,950 | A | 5/1983 | Lawson |
| 4,444,058 | A | 4/1984 | Ratigan |
| 5,999,887 | A | 12/1999 | Giannakopoulos et al. |

(Continued)

OTHER PUBLICATIONS

Gulf Cooperation Council Examination Report issued in GCC Application No. GC 2016-31981 dated Sep. 24, 2018, 4 pages.

(Continued)

*Primary Examiner* — Kiho Kim
(74) *Attorney, Agent, or Firm* — Fish & Richardson P.C.

(57) ABSTRACT

Nano-level evaluation of kerogen-rich reservoir rock is described. A nano-scale beam is formed from kerogen-rich reservoir rock. The nano-scale beam includes reservoir rock and kerogen having polymeric properties. A mechanical experiment is performed on the nano-scale beam. The mechanical experiment is imaged using a scanning electron microscope (SEM) or a transmission electron microscope (TEM). A material parameter of the kerogen in the nano-scale beam is determined based on the mechanical experiment and images obtained responsive to the imaging.

5 Claims, 40 Drawing Sheets

(56) References Cited

U.S. PATENT DOCUMENTS

| | | | |
|---|---|---|---|
| 6,866,048 B2 | 3/2005 | Mattox | |
| 7,621,173 B2 | 11/2009 | Hsu | |
| 7,654,159 B2 | 2/2010 | Enoksson | |
| 8,380,437 B2 | 2/2013 | Abousleiman et al. | |
| 8,844,366 B2 | 9/2014 | Warren | |
| 9,753,016 B1 | 9/2017 | Daugela | |
| 9,869,649 B2 | 1/2018 | Hull | |
| 9,885,691 B1 | 2/2018 | Daugela | |
| 2009/0193881 A1 | 8/2009 | Finnberg | |
| 2010/0186520 A1 | 7/2010 | Wheeler | |
| 2010/0213579 A1 | 8/2010 | Henry | |
| 2010/0279136 A1 | 11/2010 | Bonucci | |
| 2014/0048694 A1 | 2/2014 | Pomerantz | |
| 2015/0293256 A1* | 10/2015 | Dusterhoft | G01V 3/26 250/267 |
| 2017/0067836 A1 | 3/2017 | Hull et al. | |

OTHER PUBLICATIONS

Canadian Office Action issued in Canadian Application No. 2,997,353 dated Feb. 1, 2019, 3 pages.
PCT International Search Report and Written Opinion of the International Searching Authority, PCT/US2016/049971, dated Nov. 23, 2016, 12 pages.
International Search Report and Written Opinion issued in International Application No. PCT/US2017/038448 dated Aug. 22, 2017; 17 pages—new art cited.
Abad et al., "Evaluation of the Material Properties of the Multilayered Oxides formed on HCM12A using New and Novel Techniques," Manuscript Draft, Manuscript No. OXID-D-15-00019, published in 2015, 44 pages.
Abousleiman et al, "A Micromechanically Consistent Poroviscoelasticity Theory for Rock Mechanics Applications," Int. J. Rock Mech. Min. Sci. & Geomech. Abstr., vol. 30, No. 7, published in 1993, 4 pages.
Abousleiman et al, "Anisotropic Porothermoelastic Solution and Hydro-Thermal Effects on Fracture Width in Hydraulic Fracturing," Int. J. Numer. Anal. Meth. Geomech., published in 2013, 25 pages.
Abousleiman et al, "Poroviscoelastic Analysis of Borehole and Cylinder Problems," ACTA Mechanica, vol. 119, published in 1996, 21 pages.
Abousleiman et al, "SPE 110120: Geomechanics Field and Laboratory Characterization of Woodford Shale: The Next Gas Play," SPE International, SPE 110120, presented at the 2007 SPE Annual Technical Conference and Exhibition on Nov. 11-14, 2007, 14 pages.
Abousleiman et al., "GeoGenome Industry Consortium (G2IC)," JIP, 2004-2006, 6 pages.
Abousleiman et al., "Geomechanics Field Characterization of the Two Prolific U.S. Mid-West Gas Plays with Advanced Wire-Line Logging Tools," SPE International, SPE 124428, presented at 2009 SPE Annual Technical Conference and Exhibition, Oct. 4-7, 2009, 19 pages.
Abousleiman et al., "Mandel's Problem Revisited," Geotechnique, 46, No. 2, published in 1996, 9 pages.
Abousleiman et al., "Mechanical Characterization of Small Shale Samples subjected to Fluid Exposure using the Inclined Direct Shear Testing Device," Int. J. Rock Mech. & Min. Sci., vol. 47, No. 3, published in 2010, 13 pages.
Abousleiman et al., "Poroelastic Solutions in Transversely Isotropic Media for Wellbore and Cylinder," Int. J. Solids Structures, vol. 35, Nos. 34-35, published in 1998, 25 pages.
Abousleiman et al., "The Granular and Polymer Composite Nature of Kerogen-Rich Shale," Acta Geotechnica, Feb. 5, 2016, 24 pages.
Allan et al., "A Multiscale Methodology for the Analysis of Velocity Anisotropy in Organic-Rich Shale," Geophysics, vol. 80, No. 4, Jul.-Aug. 2015, 16 pages.
Ananthan et al., "Influence of Strain Softening on the Fracture of Plain Concrete Beams," Int. J. of Fracture, vol. 45, published in 1990, 25 pages.
Ballice, "Solvent Swelling Studies of Goynuk (Kerogen Type-I) and Beypazari Oil Shales (Kerogen Type-II)," Science Direct, Fuel vol. 82, published in 2003, 5 pages.
Bazant et al., "Deformation of Progressively Cracking Reinforced Concrete Beams," ACI Journal, Technical Paper, Title No. 81-26, vol. 81, No. 3, May-Jun. 1984, 11 pages.
Bazant et al., "Strain-Softening Bar and Beam: Exact Non-Local Solution," Int. J. Solids Structures, vol. 24, No. 7, published in 1988, 15 pages.
Bennett et al., "Instrumented Nanoindentation and 3D Mechanistic Modeling of a Shale at Multiple Scales," Acta Geotechnica, vol. 10, No. 21, Jan. 9, 2015; 14 pages.
Bhandari et al., "Two-Dimensional DEM Analysis of Behavior of Geogrid-Reinforced Uniform Granular Bases under a Vertical Cyclic Load, Acta Geotechnica," published in 2014, 12 pages.
Biot, "General Theory of Three-Dimensional Consolidation," Journal of Applied Physics, vol. 12, No. 2, Feb. 1941, 11 pages.
Bobko et al., "The Nanogranular Origin of Friction and Cohesion in Shale—A Strength Homogenization Approach to Interpretation of Nanoindentation Results," Int. J. Numer. Anal. Meth. Geomech., published in 2010, 23 pages.
Boskey et al., "Perspective—Collagen and Bone Strength," Journal of Bone and Mineral Research, vol. 14, No. 3, published in 1999, 6 pages.
Chen et al., "Size Effect in Micro-Scale Cantilever Beam Bending,"Acta Mech., published in 2011, 17 pages.
Chern et al., "Deformation of Progressively Cracking Partially Prestressed Concrete Beams," PCI Journal, vol. 37, No. 1, published in 1992, 11 pages.
Chupin et al., "Finite Strain Analysis of Nonuniform Deformation Inside Shear Bands in Sands," Int. J. Numer. Anal. Meth. Geomech., published in 2012, 16 pages.
Deirieh et al., "Nanochemomechanical Assessment of Shale: A Coupled WDS-Indentation Analysis," Acta Geotechnica, published in 2012, 25 pages.
Ekboil et al., "Porochemoelastic Solution for an Inclided Borehole in a Transversely Isotropic Formation," J. of Eng. Mech., ASCE, Jul. 2006, 10 pages.
Eliyahu et al., "Mechanical Properties of organic matter in shales mapped at the nanometer scale," Marine and Petroleum Geology, vol. 59, Jan. 2015, 11 pages.
Ertas et al., "Petroleum Expulsion Part 1. Theory of Kerogen Swelling in Multicomponent Solvents," Energy & Fuels, published in 2006, 6 pages.
Eseme et al., "Review of mechanical properties of oil shales: implications for exploitation and basin modeling," Oil Shale, vol. 24, No. 2, Jan. 2007, 16 pages.
Ewy, "Shale Swelling/Shrinkage and Water Content Change due to Imposed Suction and Due to Direct Brine Contact," Acta Geotechnica, published in 2014, 18 pages.
Frazer et al., "Localized Mechanical Property Assessment of SiC/SiC Composite Materials," Science Direct, Part A 70, published in 2015, 9 pages.
Gao et al., "Materials Become Insensitive to Flaws at Nanoscale: Lessons from Nature," PNAS, vol. 100, No. 10, May 13, 2003, 628 pages.
Garnero, "The Contribution of Collagen Crosslinks to Bone Strength," Int. Bone & Mineral Society, Sep. 2012, 8 pages.
Georgi et al., "Physics and Chemistry in Nanoscale Rocks", Mar. 22-26, 2015, La Jolla, California, USA, SPE Forum Series; 4 pages.
Goodman, "Introduction to Rock Mechanics," John Wiley & Sons, Chapter 3: Rock Strength and Failure Criteria; 21 pages.
Han et al., "LBM-DEM Modeling of Fluid-Solid Interaction in Porous Media," Int. J. Numer. Anal. Meth. Geomech., published in 2013, 17 pages.
Hoang et al., "Correspondence Principle Between Anisotropic Poroviscoelasticity and Poroelasticity using Micromechanics and Application to Compression of Orthotropic Rectangular Strips," Journal of Applied Physics, American Institute of Physics, vol. 112, Aug. 30, 2012; 16 pages.
Hornby et al., "Anisotropic Effective-Medium Modeling of the Elastic Properties of Shales," Geophysics, vol. 59, No. 10, Oct. 1994, 14 pages.

(56) References Cited

OTHER PUBLICATIONS

Hosemann et al, "Mechanical Characteristics of SiC Coating Layer in TRISO Fuel Particles," Journal of Nuclear Materials, vol. 442, published in 2013, 10 pages.
Hosemann et al., "An Exploratory Study to Determine Applicability of Nano-Hardness and Micro-compression Measurments for Yield Stress Estimation," Science Direct, published in 2008, 9 pages.
Iqbal et al., "In situ micro-cantilver tests to study fracture properties of NiAl single crystals," Acta Materialia, vol. 60, No. 3, Feb. 2012; 8 pages.
Iyengar et al., "Analysis of Crack Propagation in Strain-Softening Beams," Engineering Fracture Mechanics, published in 2002, 18 pages.
Jose et al., "Continuous multi cycle nanoindentation studies on compositionally graded $Ti_{1-x}Al_xN$ multilayer thin films," (XP028230250) Materials Science and Engineering: A, Elsevier, vol. 528, No. 21, Apr. 20, 2011; 7 pages.
Kelemen et al., "Petroleum Expulsion Part 2. Organic Matter Type and Maturity Effects on Kerogen Swelling by Solvents and Thermodynamic Parameters for Kerogen from Regular Solution Theory," Energy & Fuels, published in 2006, 8 pages.
Kolymbas, "Kinematics of Shear Bands," Acta Geotechnica, published in 2009, 4 pages.
Lam et al., "Experiments and Theory in Strain Gradient Elasticity," J. Mech. and Phys. of Solids, published in 2003, 32 pages.
Larsen et al., "Changes in the Cross-Link Density of Paris Basin Toarcian Kerogen During Maturation," Organic Geochemistry, published in 2002, 10 pages.
Li et al., "Mechanical Characterization of Micro/Nanoscale Structures for MEMS/NEMS Applications using Nanoindentation Techniques," Science Direct, published in 2003, 775 pages.
Liu, "Dimension effect on mechanical behavior of silicon micro—cantilver beams," Measurement, vol. 41, No. 8, Oct. 2008; 11 pages.
Liu, "Micro—cantilver Testing to Evaluate the Mechanical Properties of Thermal Barrier Coatings," 19th European Conference on Fracture (ECF19): Fracture Mechanics for Durability, Reliability and Safety; Conference Proceedings held Aug. 26-31, 2012, Kazan, Russia; 7 pages.
Mahabadi et al., "A novel approach for micro-scale characterization and modeling of geomaterials incorporating actual material heterogeneity," (XP002689941) Geophysical Research Letters, American Geophysical Union, vol. 39, No. 1, L01303, Jan. 1, 2012; 6 pages.
Mahmoud et al., "Removal of Pyrite and Different Types of Iron Sulfide Scales in Oil and Gas Wells without H2S Generation," (IPTC-18279-MS) Presented at the International Petroleum Technology Conference (IPTC), Doha, Qatar, Dec. 6-9, 2015; 8 pages.
Maio et al., "Measuring Fracture Toughness of Coatings using Focused-ion-beam-machined Microbeams," published in 2004, 4 pages.
Oliver, "An Improved Technique for Determining Hardness and Elastic Modulus using Load and Displacement Sensing Indentation Experiments," published in 1992, 20 pages.
Ortega et al., "The Effect of Particle Shape and Grain-Scale Properties of Shale: A Micromechanics Approach," Int. J. Numer. Anal. Methd. Geomech., published in 2010, 33 pages.
Ortega et al., "The Effect of the Nanogranular Nature of Shale on their Poroelastic Behavior," Acta Geotechnica, published in 2007, 28 pages.
Ortega et al., "The Nanogranular Acoustic Signature of Shale," Geophysics, vol. 74, No. 3, May-Jun. 2009, 20 pages.
Passey et al., "From Oil-Prone Source Rock to Gas-Producing Shale Reservoir—Geologic and Petrophysical Characterization of Unconventional Shale-Gas Reservoirs," Society of Petroleum Engineers International, CPS/SPE International Oil & Gas Conference and Exhibition, Beijing, China, Jun. 8-10, 2010, 29 pages.
Podio et al., "Dynamic Properties of Dry and Water-Saturated Green River Shale under Stress," Jun. 11, 1968, SPE 1825, 16 pages.
Poon et al., "An Analysis of Nanoindentation in Linearly Elastic Solids," International Journal of Solids and Structures, vol. 45, No. 24, Dec. 1, 2008; 16 pages.
Richard et al, "Slow Relaxation and Compaction of Granular Systems," Nature Materials, vol. 4, Feb. 2005, 8 pages.
Rodriguez et al., "Imagining techniques for analyzing shale pores and minerals," National Energy Technology Laboratory, Dec. 2, 2014, 44 pages.
Shin et al., "Development and Testing of Microcompression for Post Irradiation Characterization of ODS Steels," J. Nuclear Materials, published in 2014, 6 pages.
Sierra et al., "Woodford Shale Mechanical Properties and the Impacts of Lithofacies," ARMA 10-461, copyright 2010, 10 pages.
Slatt et al., "Merging Sequence Stratigraphy and Geomechanics for Unconventional Gas Shales," The Leading Edge, Mar. 2011, 8 pages.
Slatt et al., "Outcrop/Behind Outcrop (Quarry), Multiscale Characterization of the Woodford Gas Shale," copyright 2011, 22 pages.
Sone et al., "Mechanical Properties of Shale-Gas Reservoir Rocks—Part 1: Static and Dynamic Elastic Properties and Anisotropy," Geophysics, vol. 78, No. 5, Sep.-Oct. 2013, 12 pages.
Sone et al., "Mechanical properties of shale-gas reservoir rocks—Part 2: Ductile creep, brittle strength, and their relation to the elastic modulus," 2013, Geophysics, vol. 78, No. 5, 10 pages.
Ulm et al., "Material Invariant Poromechanics Properties of Shales," published in 2005, 8 pages.
Ulm et al., "The Nanogranular Nature of Shale," Acta Geotechnica, published in 2006, 12 pages.
Vanlandingham, "Review of Instrumented Indentation," Journal of Research of the National Institute of Standards and Technology, vol. 108, No. 4, Jul.-Aug. 2003; 17 pages.
Vernik et al., "Ultrasonic Velocity and Anisotropy of Hydrocarbon Source Rocks," Geophysics, vol. 57, No. 5, May 1992, 9 pages.
Wang et al., "A Numerical Study of Factors Affecting the Characterization of Nanoindent ation on Silicon," Materials Science and Engineering: A, vol. 447, No. 1, Feb. 25, 2007; 10 pages.
Wang et al., "Iron Sulfide Scale Dissolvers: How Effective Are They?" Presented at the SPE Saudi Arabia section Annual Technical Symposium and Exhibition (SPE-168063-MS), Khobar, Saudi Arabia, May 19-22, 2013; 22 pages.
Wenk et al., "Preferred Orientation and Elastic Anisotropy of Illite-Rich Shale," Geophysics, vol. 72, No. 2, Mar.-Apr. 2007, 7 pages.
Wilson et al., "Fracture testing of bulk silicon microcantilever beams subjected to a side load," Journal of Microelectromechanical Systems, vol. 5, No. 3, Sep. 1996; 9 pages.
Wurster et al., "Characterization of the fracture toughness of microsized tungsten single crystal notched specimens," Philosophical Magazine, vol. 92, No. 14, May 2012; 23 pages.
Zeszotarski et al., "Imaging and Mechanical Property Measurements of Kerogen via Nanoindentation," Geochimica et Cosmochimica Acta, vol. 68, No. 20, published in 2004, 7 pages.
Bisnovat et al., "Mechanical and petrophysical behavior of organic-rich chalk from the Judea Plains, Israel," Marine and Petroleum Geology, vol. 64, Jun. 2015, 13 pages.

* cited by examiner

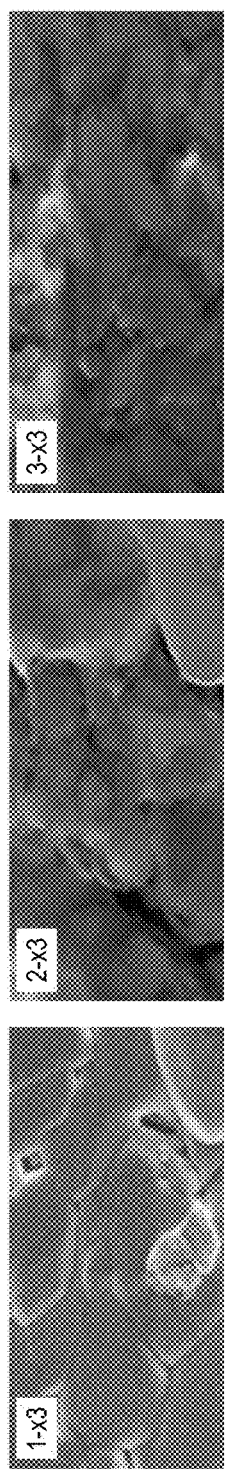
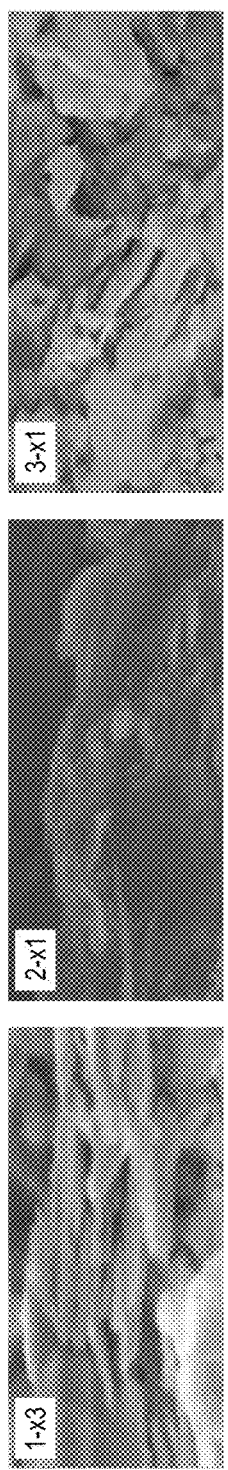
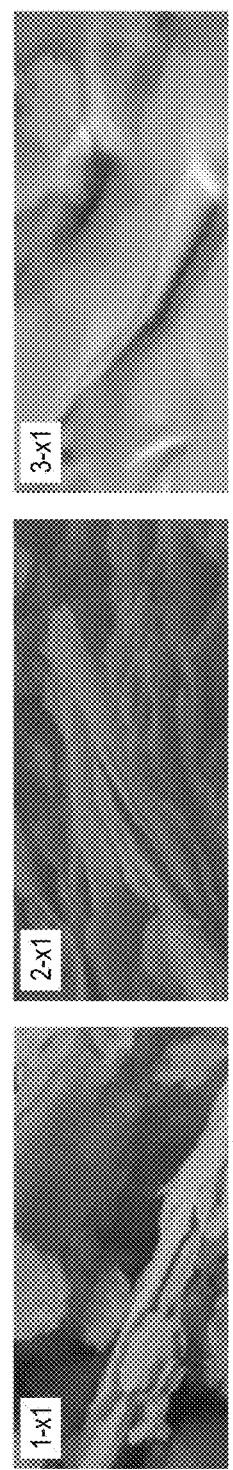
FIG. 3A  FIG. 3B  FIG. 3C
FIG. 3D  FIG. 3E  FIG. 3F
FIG. 3G  FIG. 3H  FIG. 3I

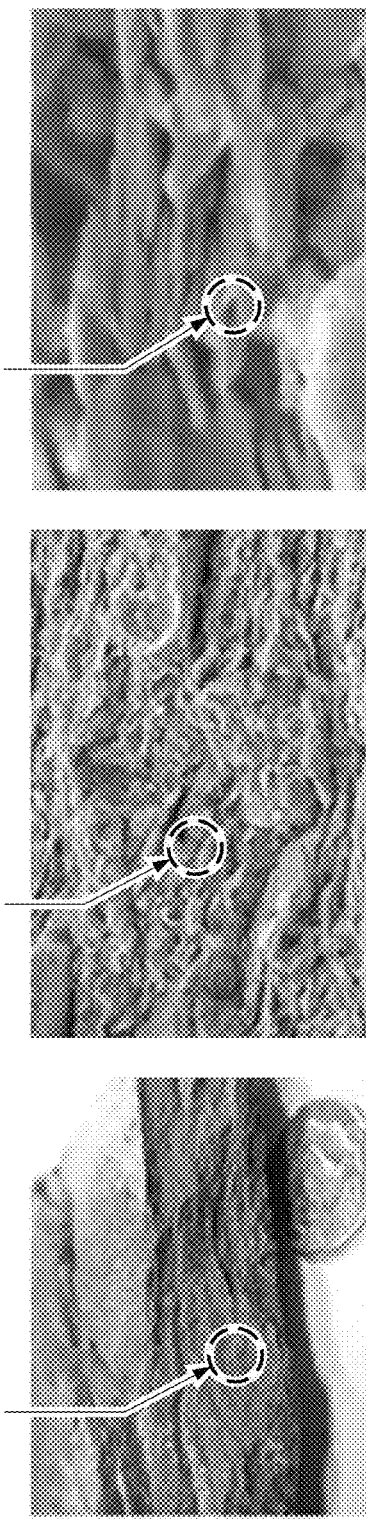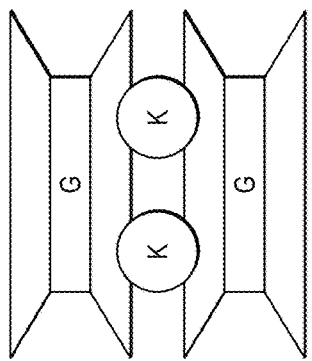
FIG. 6A  FIG. 6B  FIG. 6C  FIG. 6D

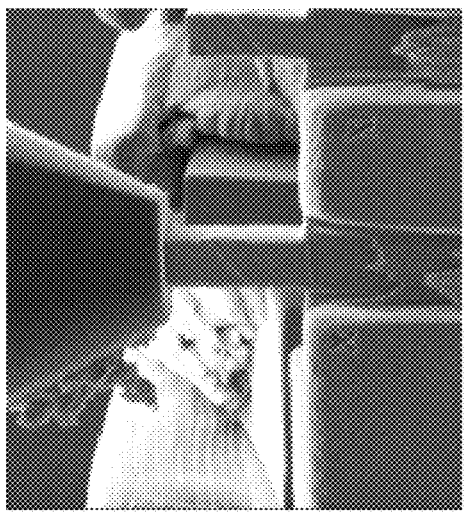
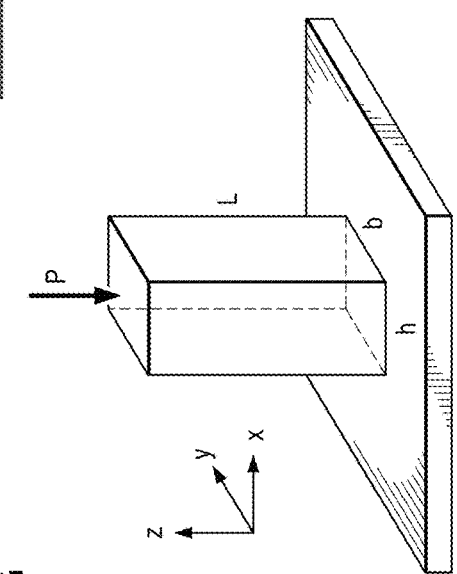
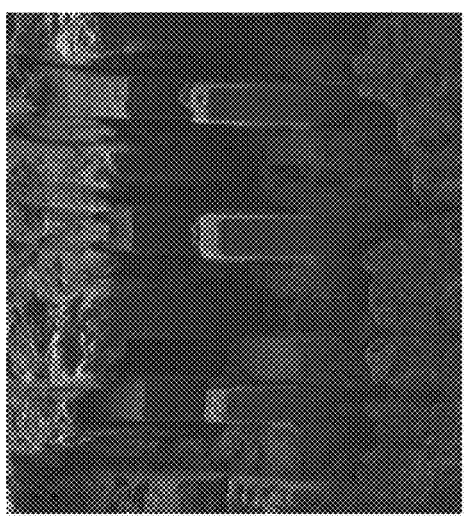
FIG. 10A
FIG. 10B
FIG. 10C

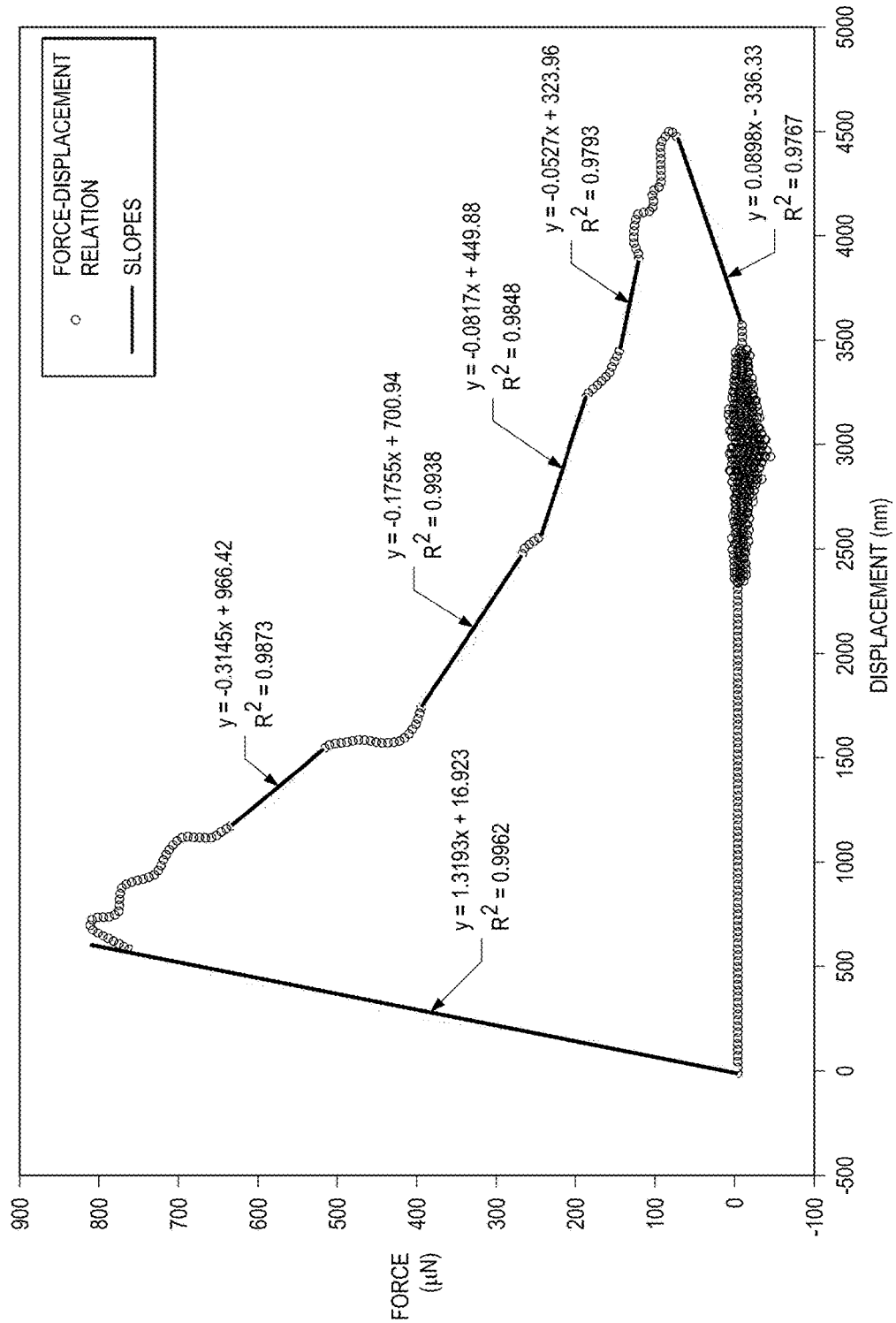

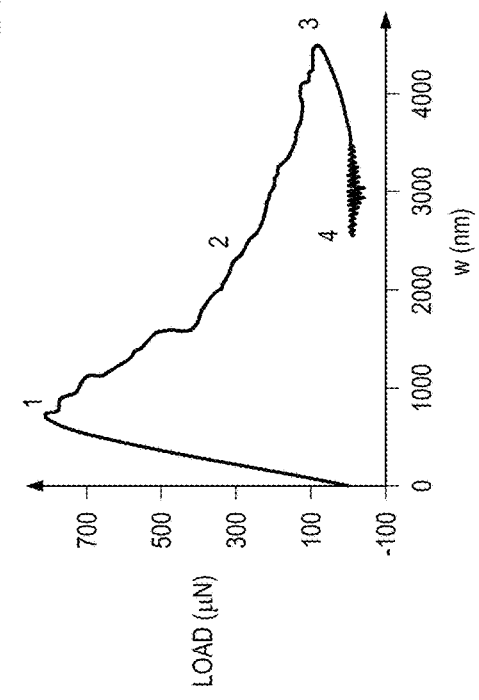
FIG. 14B
FIG. 14C
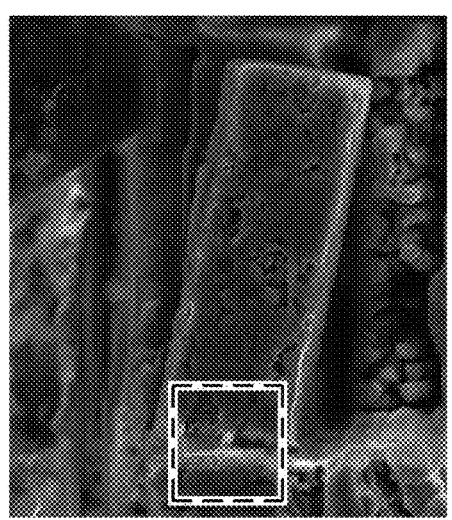
FIG. 14A

NANO-LEVEL EVALUATION OF KEROGEN-RICH RESERVOIR ROCK

CROSS-REFERENCE TO RELATED APPLICATIONS

This application is a continuation of and claims priority to U.S. application Ser. No. 15/916,027 filed on Mar. 8, 2018, which is a continuation-in-part of U.S. application Ser. No. 15/866,634, filed on Jan. 10, 2018, which is a continuation of U.S. application Ser. No. 15/250,551, filed on Aug. 29, 2016 and issued as U.S. Pat. No. 9,869,649, which claims the benefit of priority to U.S. Provisional Application Ser. No. 62/213,752, filed on Sep. 3, 2015. The contents of each of the foregoing applications is hereby incorporated by reference in entirety.

TECHNICAL FIELD

This disclosure relates to hydraulic fracturing, for example, of hydrocarbon reservoirs.

BACKGROUND

Unconventional hydrocarbon reservoirs are reservoirs with trapped hydrocarbons (for example, oil, natural gas, or combinations of them) in which the hydrocarbon mobility is limited. Extraction of hydrocarbons from such reservoirs typically involves increasing the mobility of the hydrocarbons, for example, by hydraulic fracturing. In hydraulic fracturing, a fracturing fluid (for example, proppants and one or more chemicals in an aqueous or non-aqueous base fluid) is flowed through the hydrocarbon reservoir. The fracturing fluid fractures the reservoir rock to increase mobility of the trapped hydrocarbons. Some unconventional reservoirs include an organic material called kerogen intertwined with the rock matrix.

SUMMARY

This disclosure relates to nano-level evaluation of kerogen-rich reservoir rock.

Certain aspects of the subject matter described here can be implemented as a method. A nano-scale beam is formed from kerogen-rich reservoir rock. The nano-scale beam includes reservoir rock and kerogen having polymeric properties. A maximum dimension of the nano-scale beam is at least 100 nanometer (nm) and at most 1000 nm. A tension test is performed on the nano-scale beam. The tension test is imaged using a transmission electron microscope (TEM). A material parameter of the kerogen in the nano-scale beam is determined based on results of the tension test and images obtained responsive to the imaging.

In another aspect combinable with any of the other aspects, the material parameter of the kerogen in the nano-scale beam can includes a tensile strength of the nano-scale beam.

In another aspect combinable with any of the other aspects, the tension test is a cantilever test. To perform the cantilever test, a force of the order of micro-Newtons is applied on a free-end of the nano-scale beam. To determine the material parameter, a bending of the cantilever responsive to force is measured.

In another aspect combinable with any of the other aspects, the force is applied at a rate of displacement of substantially between 1 nm/s to 100 nm/s.

In another aspect combinable with any of the other aspects, the load is applied until the nano-scale beam fails.

In another aspect combinable with any of the other aspects, heat is applied to the nano-scale beam while performing the cantilever test.

In another aspect combinable with any of the other aspects, the force can be a cantilever force applied using a nano-indenter. To perform the cantilever test, the heat is applied to the nano-indenter, and the cantilever force is applied using the nano-indenter while applying heat to the nano-indenter.

In another aspect combinable with any of the other aspects, to apply heat to the nano-scale beam, the heat is applied directly to the nano-scale beam and to the nano-indenter.

In another aspect combinable with any of the other aspects, an effect of the heat applied to the nano-scale beam on the material parameter of the kerogen in the nano-scale beam is determined.

In another aspect combinable with any of the other aspects, a mechanical property profile of the kerogen-rich reservoir rock is determined based on the effect of the heat applied to the nano-scale beam.

In another aspect combinable with any of the other aspects, the nano-scale beam includes multiple stacked shale bedding planes. The tension test is performed either parallel to or perpendicular to the plurality of stacked shale bedding planes.

In another aspect combinable with any of the other aspects, to perform the tension test parallel to the multiple stacked shale bedding planes, tension is applied in a direction that is perpendicular to a direction in which the multiple stacked shale bedding planes are stacked.

In another aspect combinable with any of the other aspects, to perform the tension test perpendicular to the multiple stacked shale bedding planes, tension is applied in a direction that is parallel to a direction in which the multiple stacked shale bedding planes are stacked.

Certain aspects of the subject matter described here can be implemented as a method. A beam is formed from a cement mixture that includes cement and a polymer. A maximum dimension of the beam is at most 1000 micrometer (μm). A mechanical experiment is performed on the beam. The mechanical experiment includes a tension test or a compression test. The mechanical experiment is imaged using a scanning electron microscope (SEM) or a transmission electron microscope (TEM). A material parameter of the polymer in the beam is determined based on results of the mechanical experiment and images obtained responsive to the imaging.

In another aspect combinable with any of the other aspects, the mechanical experiment is the tension test, and the material parameter of the polymer in the beam is a tensile strength of the beam.

In another aspect combinable with any of the other aspects, the tension test is a cantilever test. To perform the cantilever test, a force of the order of micro-Newtons is applied on a free-end of the beam. To determine the material parameter, a bending of the cantilever is measured responsive to force.

In another aspect combinable with any of the other aspects, before forming the beam, the cement mixture is treated with an organic additive configured to alter properties of the polymer in the cement mixture. An effect of organic additive on the polymer in the mixture is determined based on the material parameter of the polymer in the beam.

In another aspect combinable with any of the other aspects, the maximum dimension of the beam is at least 100 nanometer (nm).

In another aspect combinable with any of the other aspects, the beam is formed using a focused ion beam.

The details of one or more implementations of the subject matter described in this specification are set forth in the accompanying drawings and the description below. Other features, aspects, and advantages of the subject matter will become apparent from the description, the drawings, and the claims.

BRIEF DESCRIPTION OF THE DRAWINGS

FIGS. 3A-3I are scanning electron microscopy (SEM) images of kerogen-free shale.

FIGS. 6A-6D are SEM images and a schematic diagram of kerogen-free shale.

FIG. 10A is a SEM image of a micro-pillar manufactured using the FIB-SEM technique.

FIG. 10B is a schematic diagram showing dimensions of a micro-pillar.

FIG. 10C is a SEM image of a micro-pillar on which load is applied.

FIGS. 13A and 13B are detailed load versus displacement curves showing early failures with linear loading and rebounding slopes isolated.

FIG. 14A is an SEM image of a cantilever micro-beam KRS with organic rod-like material.

FIG. 14B is a SEM image of Woodford shale.

FIG. 14C is a full load versus displacement curve.

Like reference numbers and designations in the various drawings indicate like elements.

DETAILED DESCRIPTION

Unconventional reservoirs such as organic rich shale have been the subject of micro- and nano-mechanical characterization using the advances of nanotechnology. Shale and mudstones were tested using a nano-indenter while searching for the micromechanical characterization of shale rocks. One study was interested in GEOGENOMING™ clay and mudstones for applications in wellbore drilling stability and fault gauge micro-mechanics. Another study attempted to relate kerogen stiffness and anisotropy to its maturity for organic rich source shale. In these efforts, indenting at nano- and micro-scales, thus isolating mineral phases from the kerogen ones, it was concluded that kerogen stiffness is isotropic. Kerogen-free shale (KFS) was found to be strongly transversely isotropic at nano- and micro-scales. However, the kerogen stiffness and the percent volume phase, vis-à-vis the rest of the shale minerals, reduced the shale anisotropy in many instances in ultrasonic pulse velocity measurements. These early nano-indentation studies were attempts to measure the mechanics at the smallest possible "porous unit" of a mudstone rock, that is, attempting to identify what is the scale of the Representative Elementary Volume, REV, of fluid filled shale composites. Their shale samples used in these early experiments contained only "trace" levels of organic material, which means the organic matter had little effect on the overall mechanical response (the total clay content was more than 75 wt %).

Further nano-indentation studies were conducted on the organic-rich Woodford shale (≤30% clay; 10-18% kerogen) allowing the observation of the effects that the kerogen matrix has on the overall mechanical properties of KRS, including the effects on elastic and plastic behavior. The upscaling of poro-mechanical anisotropic parameters of KRS from nano-indenter characterization to macro-rock mechanics laboratory measurements and to field logging tools has also been the subject of certain studies.

Very little light has been shed on how the KRS fails in tension (such as in hydraulic fracturing) or in compression (such as in drilling) at the micro- and nano-scales as well as the effects of the kerogen polymer nature and its spatial distribution on the overall shale matrix. Classical rock mechanics testing on KRS in both tension and compression have been performed with respect to deposition modes both parallel and perpendicular to the bedding planes of the Woodford shale. However, these ASTM and ISRM standard test methods did not reveal any novelties about the failure mechanisms of the Woodford KRS.

Figure 1A:
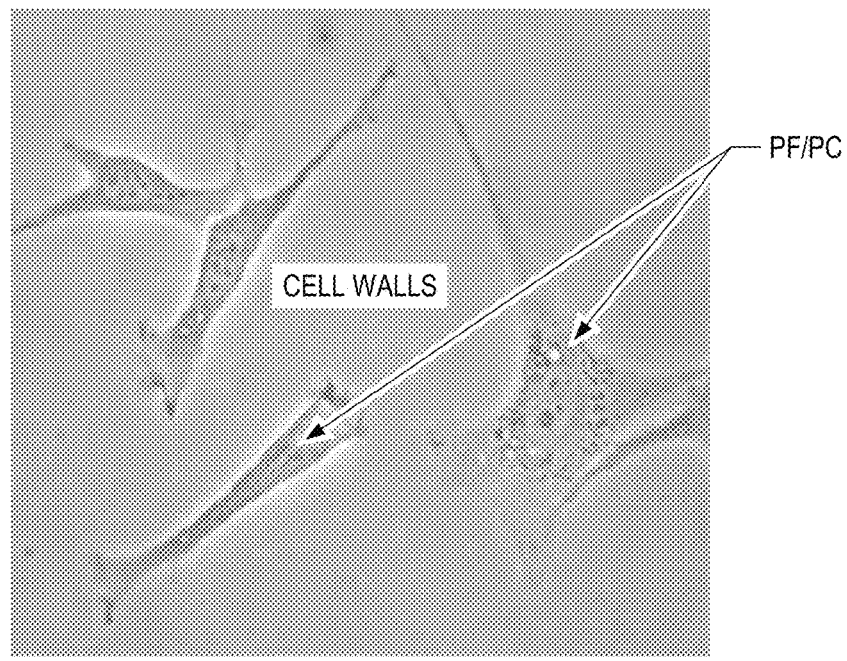
FIG. 1A is an image of porous fibroblast and porous collagen.
Figure 1B:
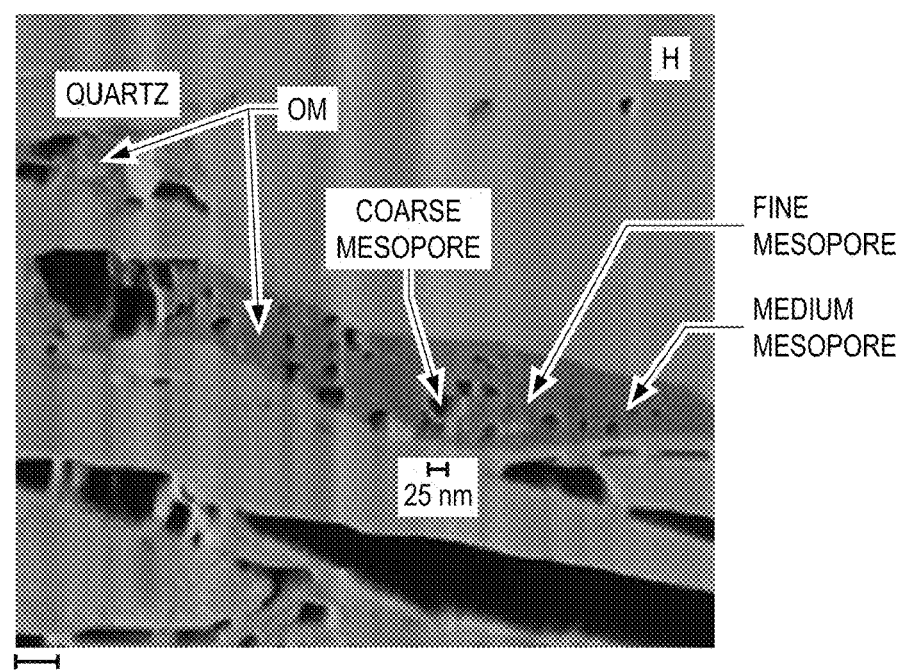
FIG. 1B is an image of porous kerogen.

This specification describes loading and failing KRS using micro-beams and micro-pillars. In some implementations, micron-sized geometries of preserved Woodford shale were manufactured via focused ion beam (FIB) under SEM, then loaded to failure via nano-indentation under the SEM. In some implementations, the loading and failing of KRS using micro-beams and micro-pillars can be performed in situ within a transmission electron microscope (TEM). Manufacturing techniques used to manufacture the test samples can include, for example, lithographic techniques, reactive ion etching, or other semiconductor manufacturing techniques. The associated forces (loads) in micro-Newtons and failures at displacements in the range of hundreds of nanometers have shown the true nature of the failure mechanisms, in compression and tension, of this composite polymer-rich porous material. It was observed that the organic phase in the tensile mode acts like a cross-linked polymer with substantial tensile strength, and a very large modulus of rupture when compared to the brittle behavior of granular shale minerals. This composite material behavior is not new to our scientific community, but kerogen tensile elastic strength has eluded our community to date. This type of behavior in natural material is also observed when measuring bone strength due to the presence of porous collagen/fibroblast as cross-linked material. The collagen/fibroblast porous nature that is embedded in bones, mimic the overall composite behavior in tension, as the porous kerogen spatially distributed within the KRS in the clay and non-clay mineral matrix as shown in FIGS. 1A and 1B. Also, organic content in bio-composites similarly augment by order of magnitudes the fracture energy of their minerals.

Figure 2A:
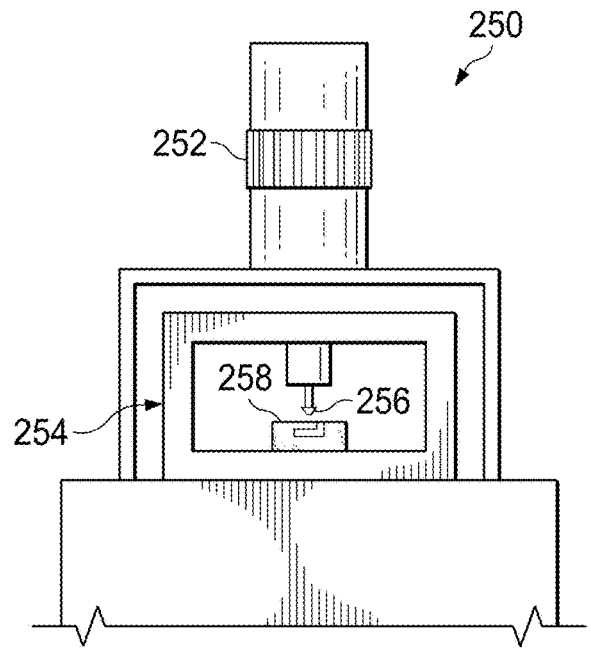
FIG. 2A is a schematic of an example testing apparatus inside an SEM.

FIG. 2A shows an example test apparatus 250 for determining properties of a micro-scale rock sample 258. A nano-indenter 254 is placed within a scanning electron microscope 252. A rock sample 258 is located within the nano-indenter 256 and can be watched while experiments are taking place. The nano-indenter tip 256 can be a variety of shape, for example, hemispherical or flat-bottomed.

Figure 2B:
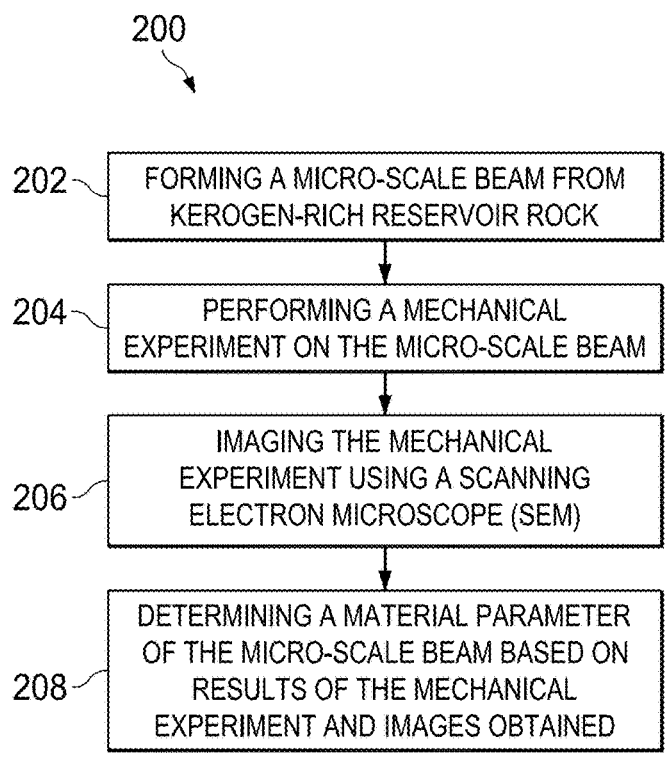
FIG. 2B is a flowchart that shows an example process for determining properties of a micro-scale rock sample.

FIG. 2B shows an example method 200 for determining properties of a micro-scale rock sample. At 202, a micro-scale beam is formed from a kerogen-rich reservoir rock. At 204, a mechanical experiment is performed on the micro-scale beam. At 206, the mechanical experiment is imaged using a scanning electron microscope (SEM). At 208, a material parameter of the micro-scale beam is determined based on results of the mechanical experiment and images obtained.

This specification also describes a preliminary two-dimensional numerical model built in order to model the loading and displacement curve in the composite shale of one of the micro-beams. The emphasis was on the kerogen volume and its intrinsic characteristics at the micro-cantilever beam support, as observed in-situ, compared to the fracture propagation and the strain softening potential of beams. The two dimensional model did capture the micro-beam load displacement curve and its corresponding modulus of toughness.

The Nano Granular Nature of Shale and its Polymer Kerogen

All shale source rock reservoirs have the major components of non-clay minerals like quartz, feldspar and plagioclase, QFP, clays such as illite, mica, smectite, and finally organic matter such as kerogen, and bitumen where the oil and gas reside. An unconventional shale reservoir with 5 wt % kerogen (~10 vol %) is considered kerogen rich. In this specification, all the various types of organic matter described above are considered to be components of kerogen, since what is of interest is the mechanics of failure of the composite organic-rich shale, and not the stage of maturity of the organic matter or the reservoir potentials. In this nano-/micro-mechanics approach, the isolated contribution of each KRS component and the role it plays in the intertwined phenomena of minerals and kerogen matrices and the different mechanisms of failure were observed. This specification describes interpretations of the experimental results and provides a preliminary numerical model based on the likely percent weight that the interlaced polymer kerogen contributes to the overall shale sample behavior.

Nano-indentation on Kerogen Free Shale (KFS): An Intrinsic Transverse Isotropic Granular Material FIGS. 3A, 3D and 3G are SEM images of a first KFS sample. The term "x3" in FIGS. 3A and 3D indicates that the sample is viewed parallel to the bedding plane. The term "x1" in FIG. 3G indicates that the sample is viewed perpendicular to the bedding plane. FIGS. 3B, 3E and 3H are SEM images of a second KFS sample. FIG. 3B indicates that the sample is viewed perpendicular to the bedding plane. FIGS. 3E and 3H indicate that the sample is viewed perpendicular to the bedding plane. FIGS. 3C, 3F and 3I are SEM images of a third KFS sample. FIG. 3C indicates that the sample is viewed perpendicular to the bedding plane. FIGS. 3F and 3I indicate that the sample is viewed perpendicular to the bedding plane. The images show sub-micron clay particles ranging between 10 nm and 100 nm in thickness in a variety of forms and shapes, ranging from sheet packages (Shale 1), to wavy flake structures (Shale 2) and highly pressed and crushed sheets (Shale 3).

Nano-indentation has been used to test small shale samples with only "trace" of kerogen present, where the volume percent is too small to alter the mechanical behavior of the shale at any scale. These shale samples studied contained 75-80 wt % clay. The shale samples were tested both parallel and perpendicular to their bedding plane with thousands of load versus displacement curves collected, which led to identifying the nano-scale material volume of anisotropy in non-organic shale. For example, a tensile strength in a direction parallel to the bedding plane is equivalent to pulling a composite network along its edges in a direction parallel to a surface of the composite network. In another example, a tensile strength in a direction perpendicular to the bedding plane is equivalent to pulling the composite network along its edges in a direction perpendicular to the surface of the composite network. The response of the composite network to the same tensile force in two different, orthogonal directions is measured. These observations concluded that the tested shale shown in FIGS. 3A-3I, are granular in nature and their anisotropic nano and micromechanical properties depends on their particle to particle contact, their packing densities, and the various stiffness of their mineral properties.

The KFS properties varied from one sample to the next, and the clay and QFP compositions varied along with their respective porosities. The granular cohesionless system of earth materials, in particular, with compaction histories, "memory" and compacted densities, are very complex processes when it comes to their mechanical properties. Clay-bearing sedimentary rocks, such as shale, formed under even more complex geological processes, are mechanistically even more complex. The role of their mineral composition in the overall mechanical property characterization has been the subject of many studies. The KFS in the SEM images in FIGS. 3A-3I were nano-indented, in-bedding and perpendicular to bedding, and exhibited clear mechanical anisotropy at these scales without any effects from organic matter.

Figure 4:
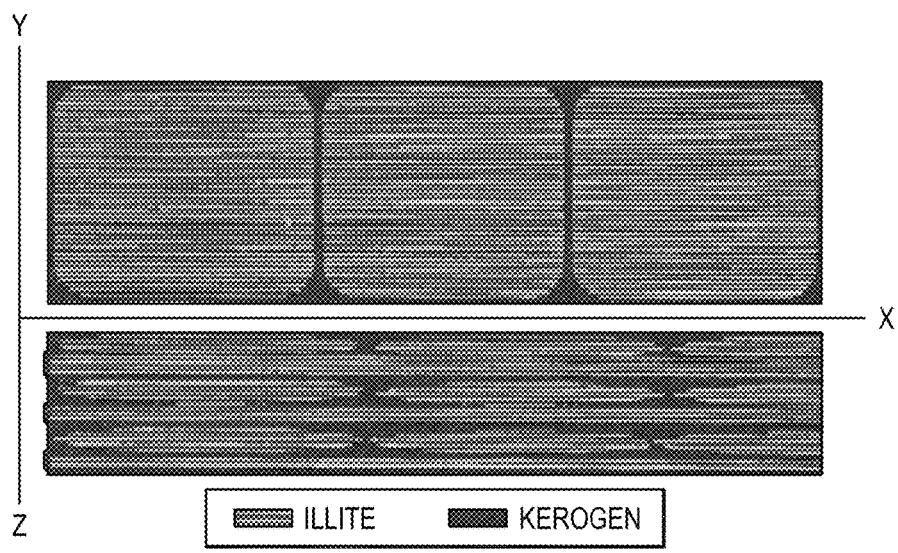
FIG. 4 is a schematic of complex layering of illite and kerogen in kerogen-rich shale.

The Intertwined View of Kerogen Rich Shale (KRS) as a Transverse Isotropic Composite Shale anisotropy has been known and modeled in our mechanistic approaches from early on, as a fluid saturated porous media exhibiting transverse isotropy likely due to mode of deposition, bedding planes, micro-fractures or micro- and nano-clay shape or both and packing porosity as described in the above section. Experimental results, particularly acoustic measurements, provided early evidence of shale transverse anisotropy. However, for source rock KRS, the acoustic measurements have attributed shale anisotropy not only to fractures and bedding planes but also to the presence of kerogen interlayered with illite clay minerals as shown in FIG. 4. Previous research has paved the way for geomechanics anisotropy modeling of shale in wellbore stability analysis, reservoir compaction simulation, and shale laboratory testing characterization. However, kerogen could not be definitively pinned as the culprit for anisotropy at all scales. KFS has shown intrinsic anisotropy and in many instances even higher than KRS anisotropy at micro and macro scales.

However, when the conceived structure of clay and kerogen combined as shown in FIG. 4, is taken to failure by tensile or compressive forces, it will be extremely hard to imagine let alone to model the various phases and how will they interact with the rest of the shale matrix. Kerogen as a polymer has intrinsic mechanical properties for elastic behavior and its own material properties at plastic yield. The limitation of an isotropic plastic model to be able to model the plastic yield from nano-indentation of the KRS has been addressed in previous research. The anisotropic stiffness parameters and the nature of organic free and or organic rich shale and their intrinsic transverse isotropy from nano- to macro-scales have been addressed in detail elsewhere.

Example of a Shale Formation

This specification describes nano- and micro-scale Woodford KRS taken to failure in tension and compression. As background, a brief description of the geological setting is provided below.

Figure 5A:
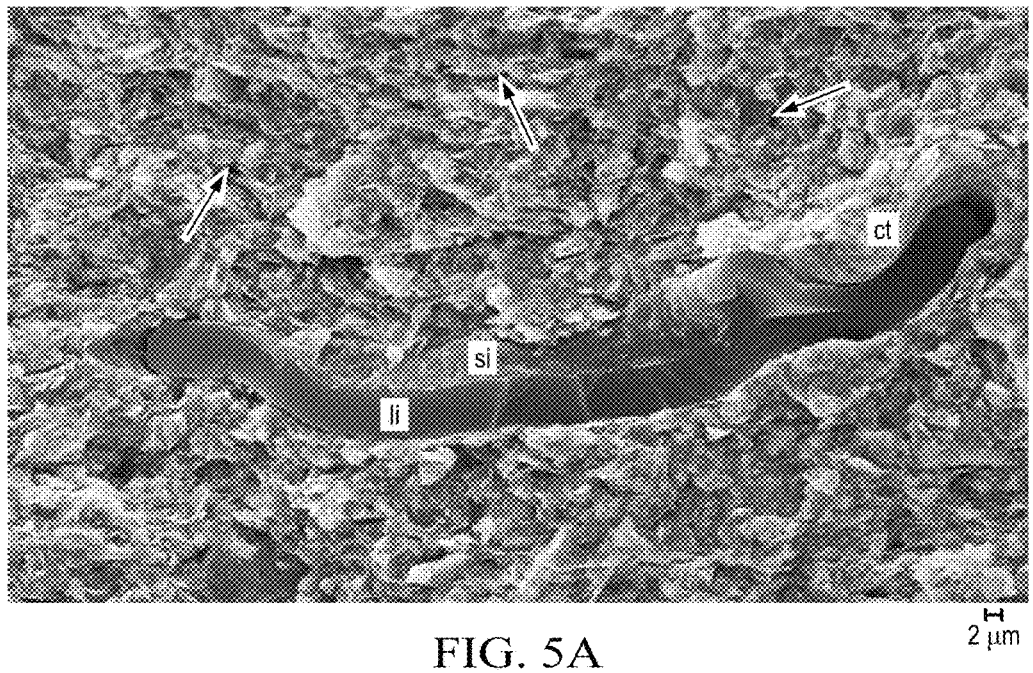
FIGS. 5A and 5B are SEM images of an example shale formation including kerogen-rich shale.
Figure 5B:
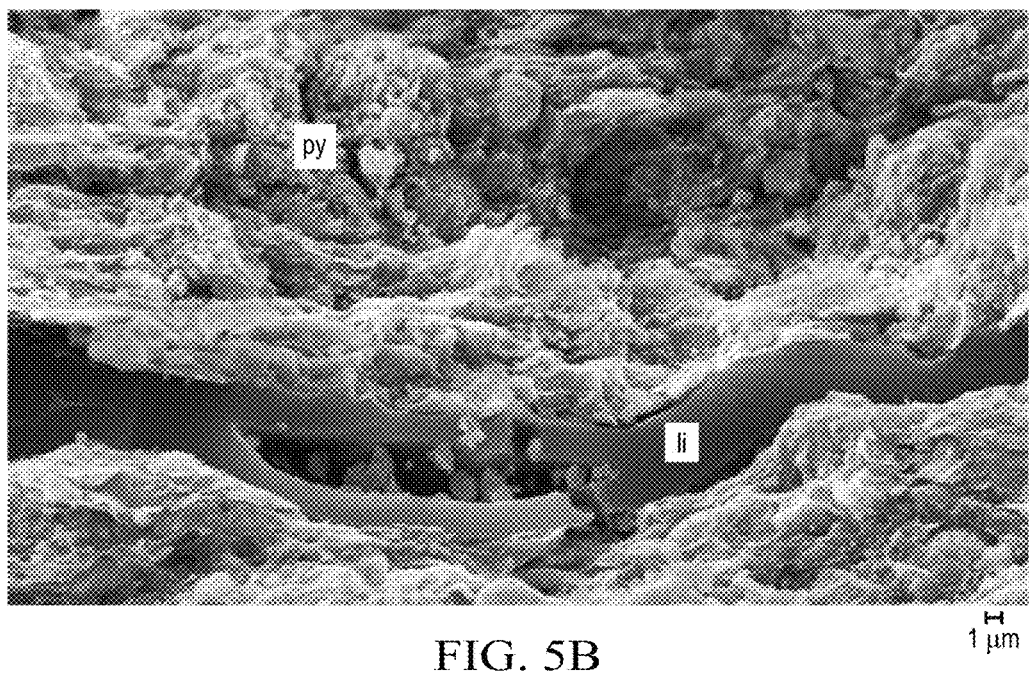

The Woodford shale formation, deposited during the lower Missisipian and upper Devonian period in an anaerobic marine environment, is found throughout the central part of the U.S. Midwest. The formation has long been known to be one of the major source rocks of the region, and for the past decade it has been a great source of energy in gas and oil. Woodford shale has high quartz content as revealed by X-ray diffraction (XRD) analysis, greater than 20% in total porosity, and permeabilities ranging from 80-40 nano-Darcys. While it is typical of source rock shale to have kerogen dispersed in its structures, the Woodford shows pronounced intertwined kerogen strings shown in two-dimensions when compared to the overall granular mineral matrix. FIGS. 5A and 5B show very complex shapes of organic material (kerogen) in the Woodford. The SEM images of Woodford shale highlight the intertwined nature of minerals and kerogen (black polymer-like ribbons). The scale of the ribbons is tens of micro-meters.

The heterogeneity of the Woodford KRS, like all source shale, is due among many reasons, to local non-clay minerals such as quartz, calcite and pyrite, and clay minerals intertwined with kerogen string-shaped components at nano, micro and macro levels. Similar to the multiscale structure of KFS a complementary KRS multiscale mechanistic structure, based on SEM images, is shown in FIGS. 6A-6H.

Figure 6E:
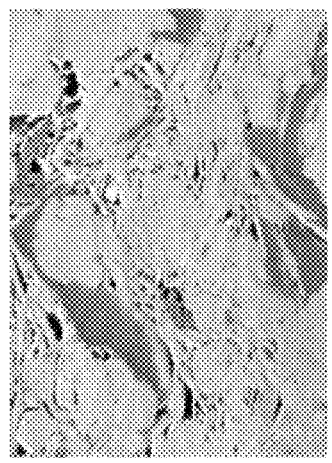
FIGS. 6E-6H are SEM images and a schematic diagram of kerogen-rich shale.
Figure 6F:
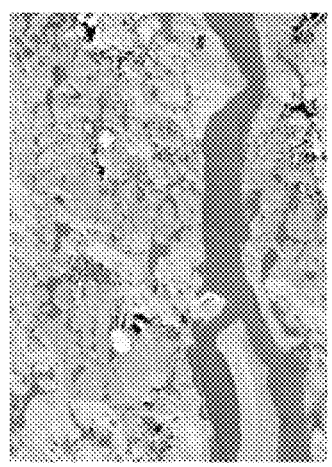
Figure 6G:
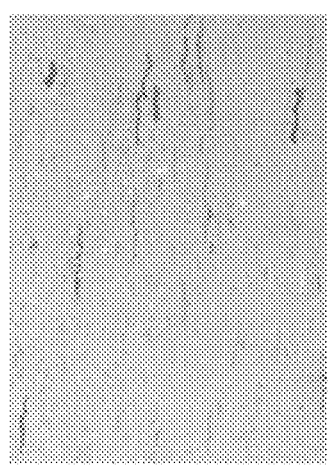
Figure 6H:
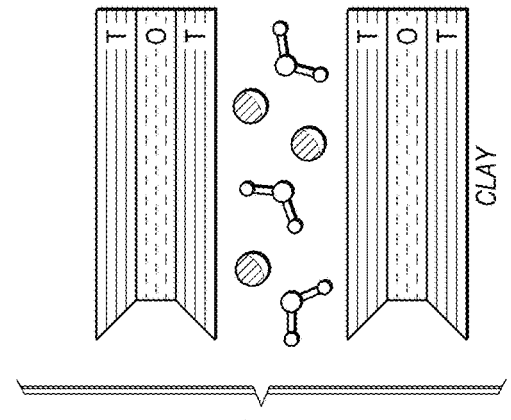
Figure 6H:
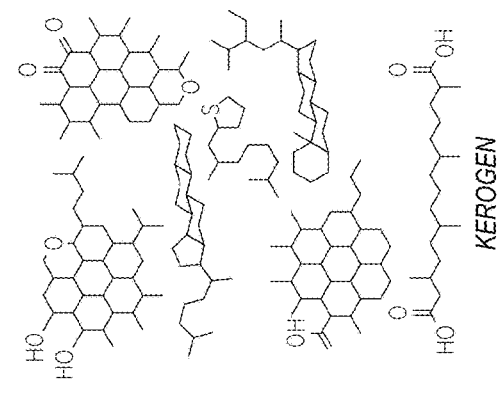

FIG. 6A is a macro-level SEM image of kerogen-free shale, for example, porous clay-silt inclusion composite, taken at a scale of greater than $10^{-3}$ m. FIG. 6B is a micro-level SEM image of a portion of the kerogen-free shale shown in FIG. 6A taken at a scale of greater than $10^{-5}$ m. FIG. 6C is a sub-micro-level SEM image of a portion of the kerogen-free shale shown in FIG. 6B taken at a scale of greater than $10^{-7}$ m. FIG. 6D is a schematic drawing of a portion of the kerogen-free shale shown in FIG. 6C drawn at a scale greater than $10^{-9}$ m. FIG. 6E is a macro-level SEM image of kerogen-rich shale, for example, layered composite shale with clay/quartz mix (light gray) and organic layers (dark gray), taken at a scale of greater than $10^{-3}$ m. FIG. 6F is a micro-level SEM image of a portion of the kerogen-rich shale shown in FIG. 6E taken at a scale of greater than $10^{-5}$ m. The image shows kerogen and micro-pores distributed throughout the mineral matrix. FIG. 6G is a sub-micro-level SEM image of a portion of the kerogen-rich shale shown in FIG. 6F taken at a scale of greater than $10^{-7}$ m. The image shows nano-porous minerals interwoven with nano-porous organic matter. FIG. 6H is a schematic drawing of a portion of the kerogen-rich shale shown in FIG. 6G at a scale greater than $10^{-9}$ m. The schematic diagram shows elementary components, namely, clays such as illite, smectite, etc., and organic molecules, for example, kerogen.

In compiling this micro to macro structure with micro-bedding planes and micro-fractures shown at level II, the failure mechanisms of such composite are very complex. For example, in tensile loadings, the polymer and rubber-like kerogen embedded in the shale matrix, at all scales, will augment the tensile rupture (modulus of toughness) of the granular fractured structure matrix.

Figure 7:
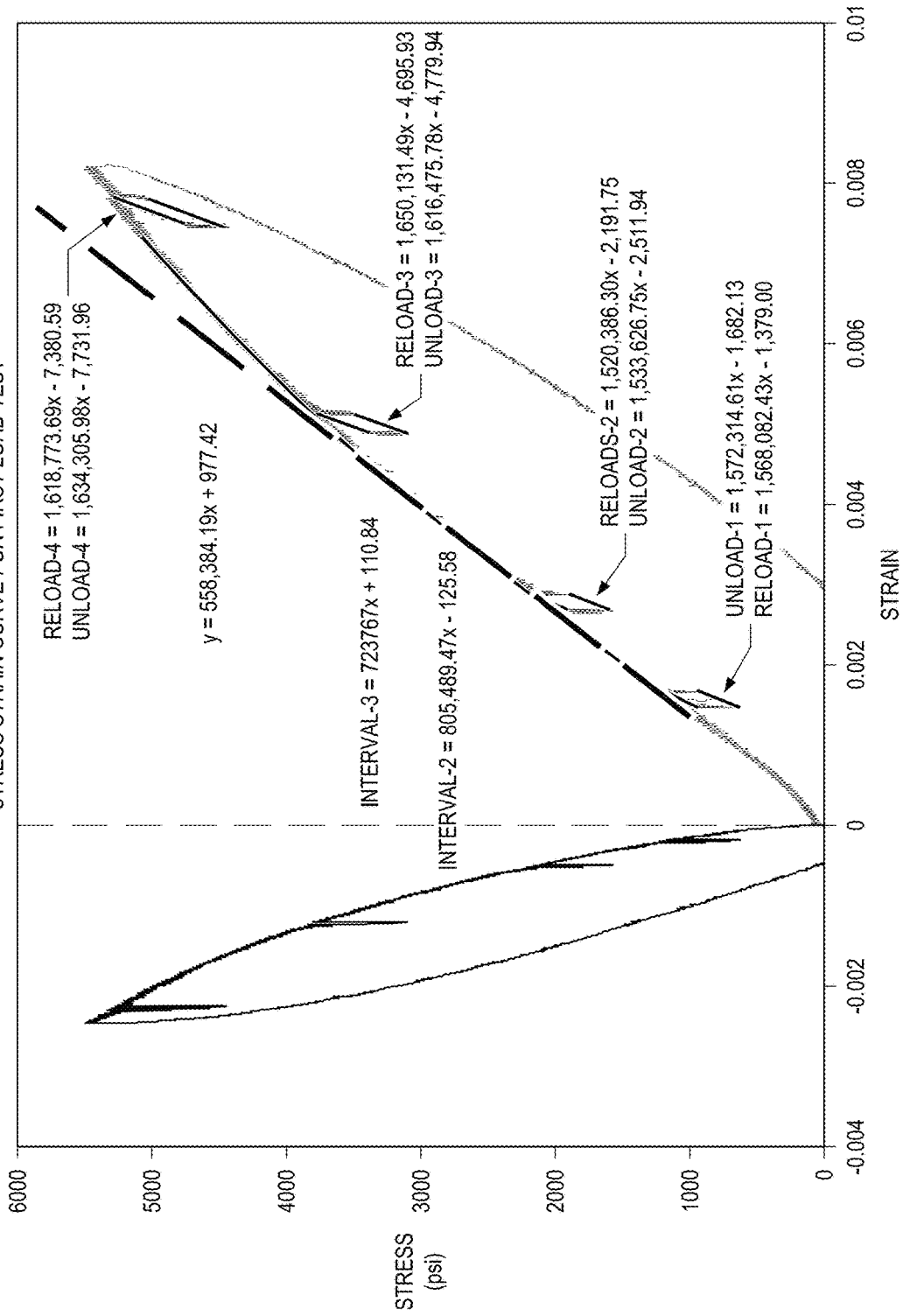
FIG. 7 is a plot of stress versus strain and load/unloading small strain Young's Moduli.

Macro-Scale Testing of Shale in Light of Kerogen Content and Composite Nature of KRS In this section, the data and the macro-scale testing conducted on the same preserved Woodford is revisited for many details that previously were missed since kerogen content, and the composite nature of KRS, was not considered in the previous data interpretations. In the previous study, only the classical geomechanics approaches were considered with corresponding mechanical parameters. FIG. 7 shows the loading and unloading up to failure of an ASTM 2"×4" standard of the preserved Woodford KRS in an unconfined compressive loading configuration. The unconfined compressive strength value is more than 5000 psi in compression with the large sample deformation close to 0.8% strain. The axial and radial stress/strain curves show the slightly plastic yield deformation starting at the third round of loading/unloading (the straight dotted line on the axial deformation) eventually masked by piece-wise partly linear slope to eventually undergo brittle failure. Yet the small strain Young's moduli shown in Table 1 (below) at the third and fourth cycles were unaffected by the stress yield. This bilinear elastic behavior, followed by a brittle failure, is intriguing and is difficult to explain, considering single granular phase behavior.

TABLE 1

Young's Modulus for small strain measurements for Woodford shale sample. Another observation is that the Young's moduli measured at loading/unloading cycles were more than 50% larger than the overall Young's modulus of the full testing load range shown in Table 2.

| Axial Stress (psi) | Cycling E (Mpsi) |
| --- | --- |
| 1250 | 1.57 |
| 2300 | 1.53 |
| 3700 | 1.62 |
| 5500 | 1.62 |

TABLE 2

ASTM measurements. Sample 166-2 to 166-6

| Strength (psi) | 1800 |
| --- | --- |
| E (kpsi) | 660 |
| ☐ | 0.3 |

The value of the dynamic Young's moduli calculated from the compressional and shear waves velocities were 10-15% different from the loading/unloading small strain cycles, thus confirming the granular porous nature behavior of this shale when undergoing compressive small loads.

Figure 8A:
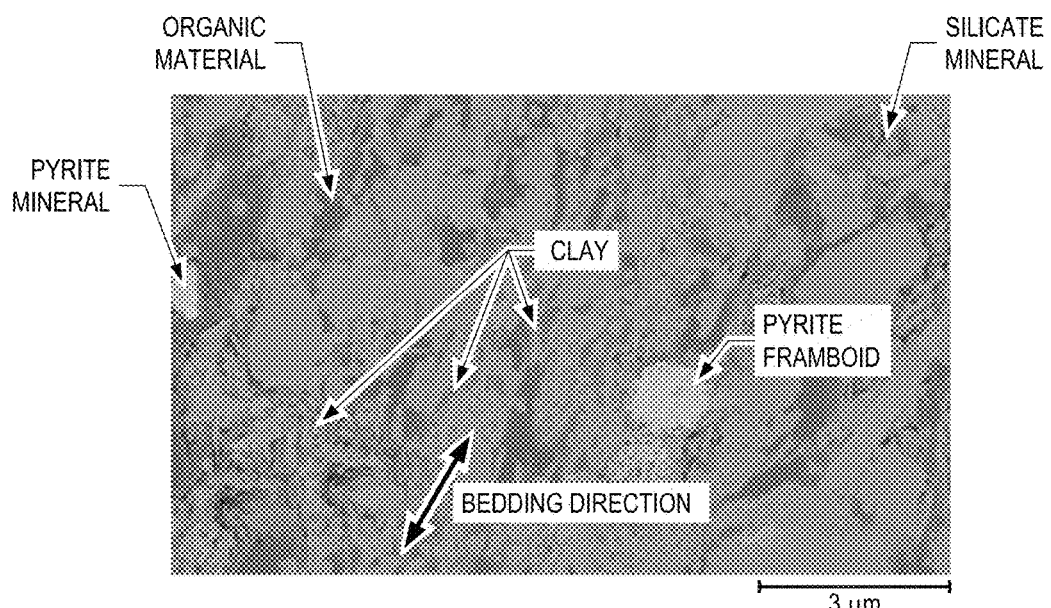
FIGS. 8A and 8B are SEM images of shale.
Figure 8B:
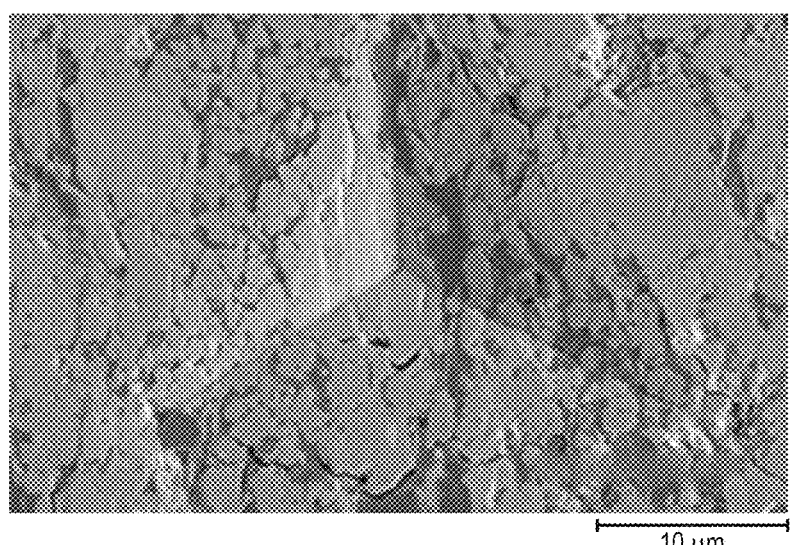

Recent data summarizes another large campaign of nano-indentation testing on these same horizons of the preserved Woodford KRS. The full sweep of tests on shale samples, both parallel and perpendicular to beddings, showed that the organic matters have anisotropic stiffness, and much smaller stiffness values than reported previously in the plane parallel to beddings. Recent research indicated that damage may have occurred during cutting and polishing, due to heat, altering the inherent kerogen anisotropy, and that the kerogen rebound when load was removed and some permanent deformation (plastic) remained as evidenced by the indentation imprint. FIGS. 8A and 8B provide much clearer SEM images that, illustrating clearly what was called " . . . indentation into a highly heterogeneous region," showing a large percentage of the organic matter and minerals and being simultaneously indented. FIG. 8A shows a polished surface with organic material which includes 1 μm-sized diameter pyrite framboids, silicate, clays, etc. FIG. 8B shows a similar region which has been indented. The final area projected after the indent imprint is roughly 450 μm². The preliminary conclusion of these above described experiments is that the organic matter in the source shale needs to be somehow reinvestigated within the overall framework of the porous shale.

Example of an Experiment to Prepare a Kerogen-Rich Shale (KRS) Sample

Focused Ion Beam (FIB)—Scanning Electron Microscopy (SEM) sample preparation of specific geometries such as micro-pillars and micro-cantilevers of KRS are described here. In some implementations, four micro-beams and three micro-pillars were milled and prepared for in-situ testing.

Figure 9A:
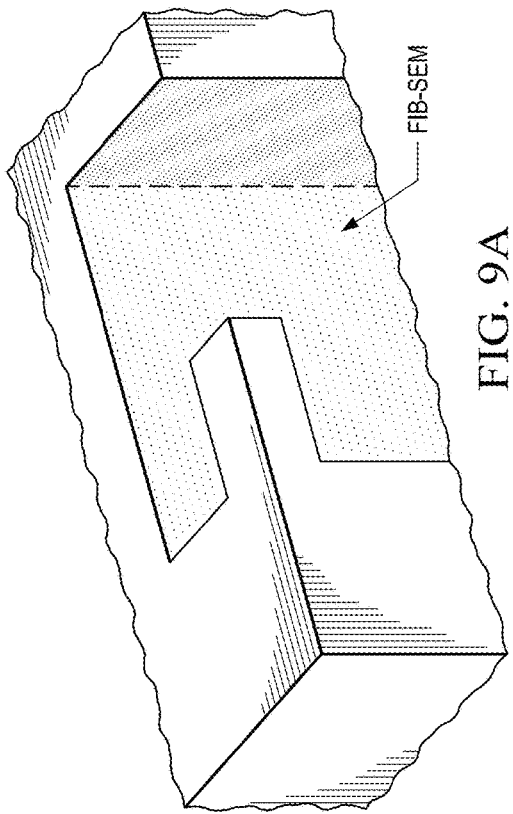
FIG. 9A is a schematic diagram of a FIB-SEM sample.
Figure 26B:
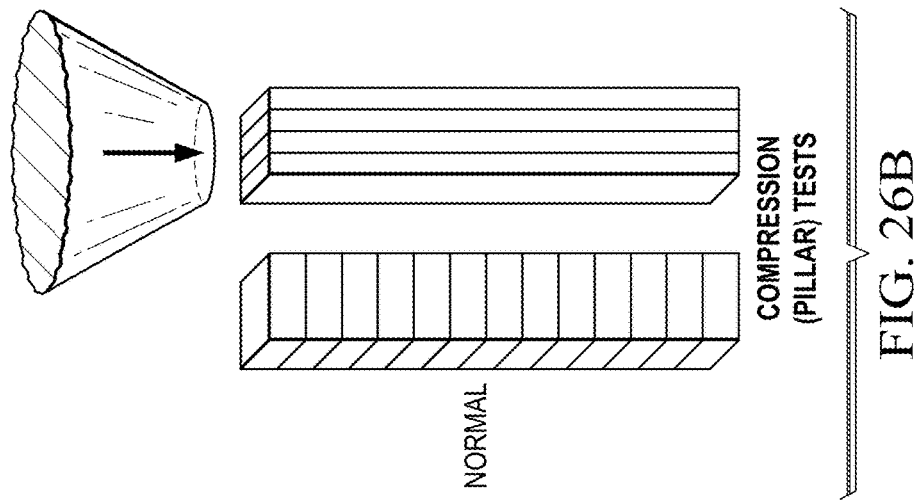
FIG. 26A-26B are schematic diagrams of indenter tips at different orientations relative to shale bedding planes for a tension and compression test respectively.
Figure 26A:
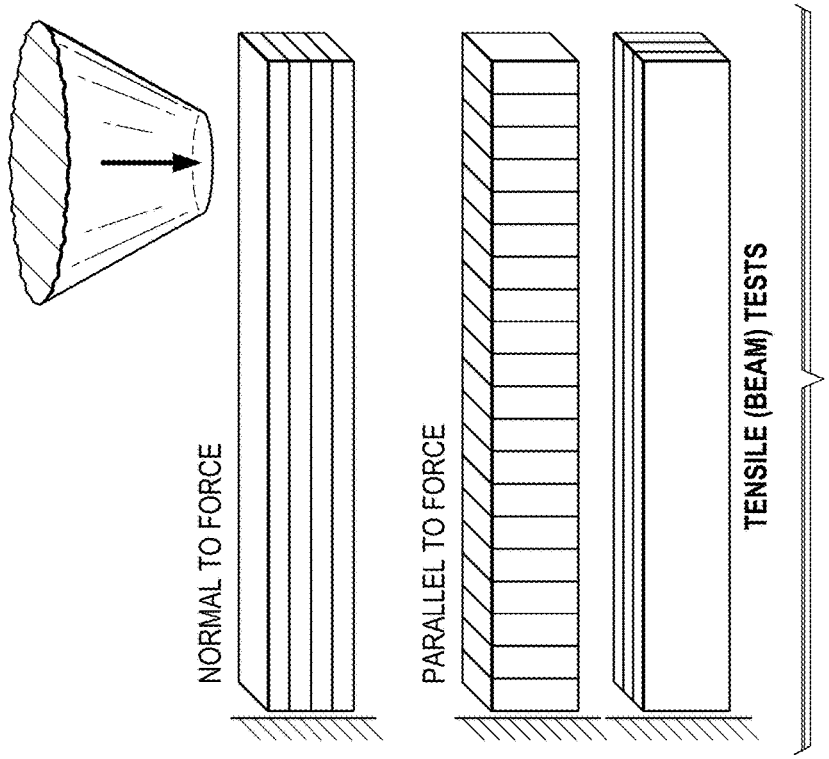

Example of Cantilever Testing KRS Micro-Beams Using a Pico-Indenter (PI-85) in the FIB-SEM A sample with dimensions of 1 cm×1 cm×0.4 cm was cut from a preserved Woodford KRS core. A sharp 90° edge was created by mechanical polishing using standard silicon carbide paper up to 4000 grit followed by polishing with 1 μm diamond grit. A Quanta 3D field emission gun (FEG) with FIB-SEM was used to prepare the micro-beams. FIB surface milling was used to clean the surface for better sample imaging as well as to prepare the desired micro-geometries. Four micro-beams were manufactured using the FIB procedure according to the S.G. Roberts method. While the beams in this experiment were manufactured according to the S.G. Roberts method, other manufacturing techniques, such as lithographic techniques, reactive ion etching, or other semiconductor manufacturing techniques, can be used. Each shale micro-beam was shaped by cutting trenches on all three sides with widths of 20 μm and depths of 10 μm using a 15 nA beam current, resulting in a U-shaped trench. The geometry was then refined by applying a 1 nA beam current. Afterwards, the sample was tilted to 45° along the length axis to shape the cantilever. The base of the cantilever was undercut from both sides using a 3 nA beam current. The resulting cantilever geometry is shown schematically in FIG. 9A, with the corresponding SEM images of three of the four micro-cantilever beams shown in FIG. 9B. It should be noted that this sample size is still well above the REV of composite shale. As shown in FIG. 26A and FIG. 26B, the beams can be manufactured with varying orientations relative to the shale bedding planes, such as perpendicular to the force of the indenter tip 256 or parallel to the force of the indenter tip 256. Manufacturing the beams at the varying orientations can allow studying anisotropy of the beams and upscaling the anisotropy to larger KRS samples.

Figure 9C:
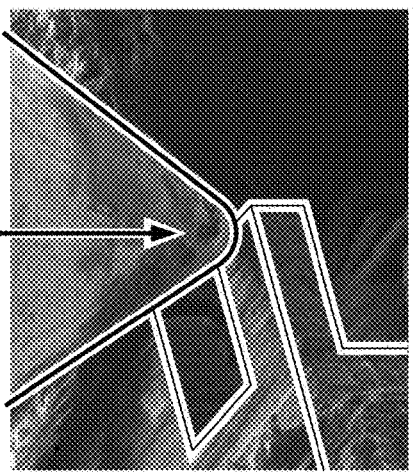
FIG. 9C is a SEM image of a cantilever load being applied on a FIB-SEM sample.
Figure 9D:
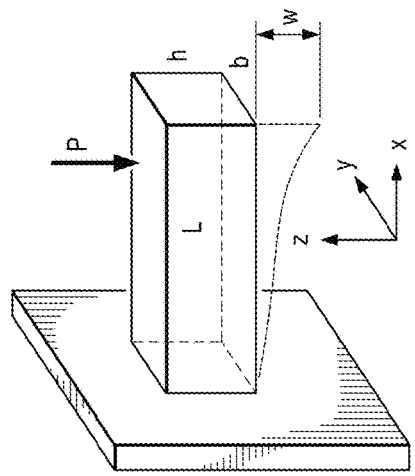
FIG. 9D is a schematic diagram of a cantilever load being applied on a FIB-SEM sample.

A Hysitron Pi-85 Pico-indenter was used to load the micro-beams under displacement control mode, at a rate 10 nm/s. The indenter tip is a flat circular punch geometry, with a diameter of 5 μm. All loading experiments were performed in situ under the SEM, where loading of the micro-cantilever beams continued until failure. The indenter tip was placed at the end of the beam, centered along the y-axis as shown in the SEM in FIG. 9C. Load and displacement data were collected in real-time. FIG. 9D is a schematic diagram showing the micro-experiment with dimensions.

During the experiment, a force (micro-Newtons) is applied to the beam or pillar through the nano-indenter tip. As the force is applied, the beam or pillar deforms (meaning the indenter tip is displaced in nanometers). Both the force and displacement are captured by the nano-indenter software throughout the experiment. Typically the rate of displacement is controlled (for example, 1-100 nm/s, 5-20 nm/s or other rate of displacement) while the force is applied to such a degree as to maintain this displacement rate. Because this experiment is performed inside a scanning electron microscope (SEM), the fourth parameter captured (beyond force, displacement, and time) is an SEM image. In fact, the SEM images are captured throughout the entire loading experiment as a movie of the entire experiment. Finally, additional analysis of the micro-beam and micro-pillar can also be performed with energy dispersive x-ray spectroscopy (EDS) while the sample is inside the SEM. This measurement provides the chemical (elemental) composition of the sample. It can be performed pre-loading, post-failure, or in some configurations, during the loading.

Earlier, it was illustrated from macro measurements on 2×4" samples that the loading/unloading Young's Moduli differed from the large strain Young's Modulus by more than 50% but are within 10% of the dynamic measurements. Also, the values of Young's moduli obtained by nano-indentation on porous multiphase material are close in value to the small strain deformation and to the ultra-pulse velocity measurements. However, when a solid metallic beam with micron-sized dimensions is subjected to loading, there is strong evidence that size effects come into play. This phenomenon has been elaborated on and theoretical results have been obtained corresponding to an intrinsic length scale effects on the overall deflection, w, of a solid micro-cantilever beam with intrinsic length scale, $l_{FE}$ that is found by calibrating a typical beam thickness with the experimental suite of results. The expression relevant to the experiments described here is shown in Equation (1).

$$w = \frac{Px^2(3L - x)}{6E(I + bhl_{FE}^2)} \quad (1)$$

In Equation (1), I is the moment of inertia for the micro-cantilever beam prismatic cross section. The length of the cantilever beam runs along the x-axis, and the position of the indenter tip along that axis is denoted as x. It is assumed that that x=L because they are very similar. The parameter E is the Young's modulus, which is a measure of the stiffness. It is reported in units of GPa. Equation (1) provided satisfactory results when used to analyze experimental measurements. However, Equation (1) may need to be modified for a granular multi-porous structured material intertwined with organic matter. The discovery is that when we assumed $l_{FE}$=0 for Equation (1), where it turns into the expression for the classical theory of beams, the micro-cantilever beam Young's moduli was within 10% error from the ones shown in Table 1. Indeed, results calculated from the classical theory for the stiffness expression (Equation (2)) match the nano-indenter results as well as the small strain loading/unloading of FIG. 7, and the corresponding ultra-pulse velocity measurements using the compressional and shear wave velocities.

$$E = \frac{PL^3}{3wI} \quad (2)$$

Example of Compression Testing KRS Micro-Pillars Using a Pico-Indenter (PI-85) in the FIB-SEM As shown in FIG. 10A, square micro-pillars with minimal taper were manufactured in the FIB instrument (Quanta 3D FEG) with successively lower beam currents (5 nA down to 0.3 nA at 30 kV) to achieve the geometries shown in FIG. 10B. Alternatively, the micro-pillars can have other cross-sectional shapes. For example, the micro-pillars can be round. The milling procedure followed the methods of earlier works. To achieve the square geometry, the sample was tilted by ±2° with respect to the incident ion beam in order to mill the side surfaces of the pillar by grazing incident ions. The aspect ratio (micro-pillar height divided by width) was set close to three to one. These dimensions may vary slightly, eventually, if these tests are to be standardized for porous natural material such as shale. While the beams in this experiment were manufactured in the FIB instrument, other manufacturing techniques, such as lithographic techniques, reactive ion etching, or other semiconductor manufacturing techniques, can be used.

Figure 9B:
FIG. 9B is a SEM image of a FIB-SEM sample.

FIG. 10C shows a load being applied to a micro-pillar. A different Hysitron indenter was used to uni-axially compress the micro-pillars using a diamond flat punch tip indenter (60° conical, 10 μm diameter flat end) as shown in FIG. 9C. The micro-pillars were loaded at a predetermined displacement rate until failure. FIG. 9B provides a schematic of the micro-pillar with dimensions of b, h, and L and applied force P. The compression of the micro-pillar samples under the nano-indenter can be described by the classic compressional stress-strain relationship.

Micro-Beam Testing

Figure 11:
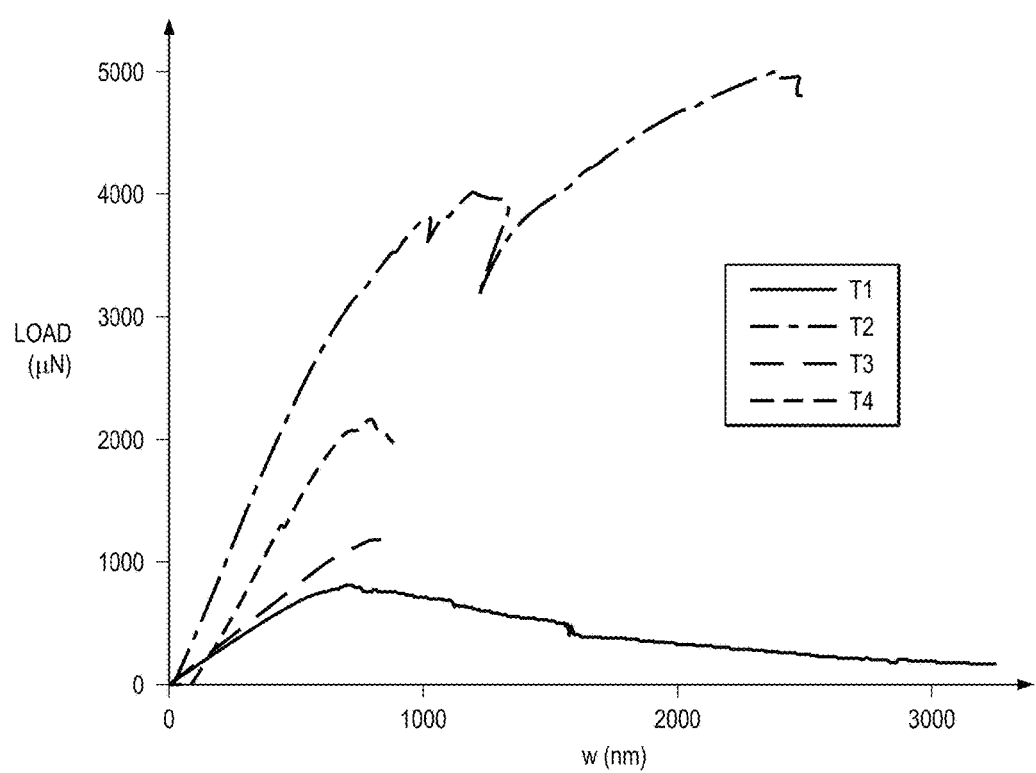
FIG. 11 shows a load versus displacement curve for four micro-beams.

FIG. 11 shows a load v/s displacement curve for four micro-beams. Four micron-sized beams were milled to load and fail Woodford shale in tensile mode. Each test was performed inside the SEM with a small-scale nano-indenter, and movies of the loading and failure were captured in real time during the experiment. This unique setup provided not only the ability to load and fracture micro-scale KRS structures but also the advantage of visualizing the initiation of a fracture in the tensile zone, then propagation, and ultimate failure while correlating these phenomena with the force-displacement plots collected during the experiments. The load-displacement curves (FIG. 11) show that samples T3 and T4 failed in brittle modes while samples T1 and T2 showed plastic deformation before failure. Samples T1 and T2 showed strain softening and strain hardening behavior, respectively before ductile failure. Samples T3 and T4 showed brittle failure with little or no yield.

Figure 21A:
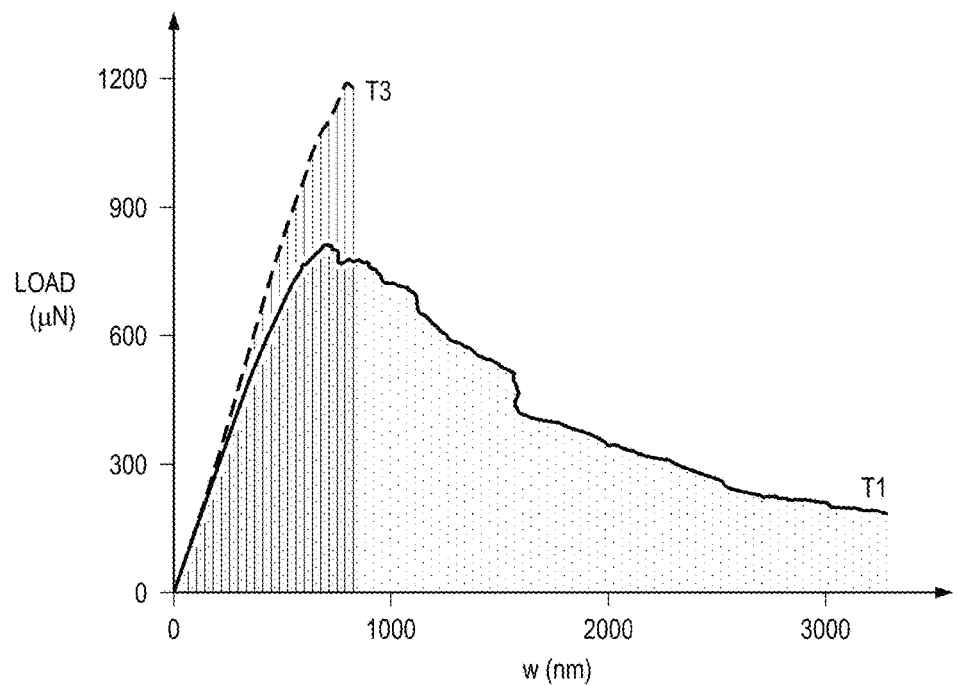
FIGS. 21A and 21B show moduli of ruptures of granular shale (T3) compared to kerogen elastomer cross-linked polymer in T1 and T2.
Figure 21B:
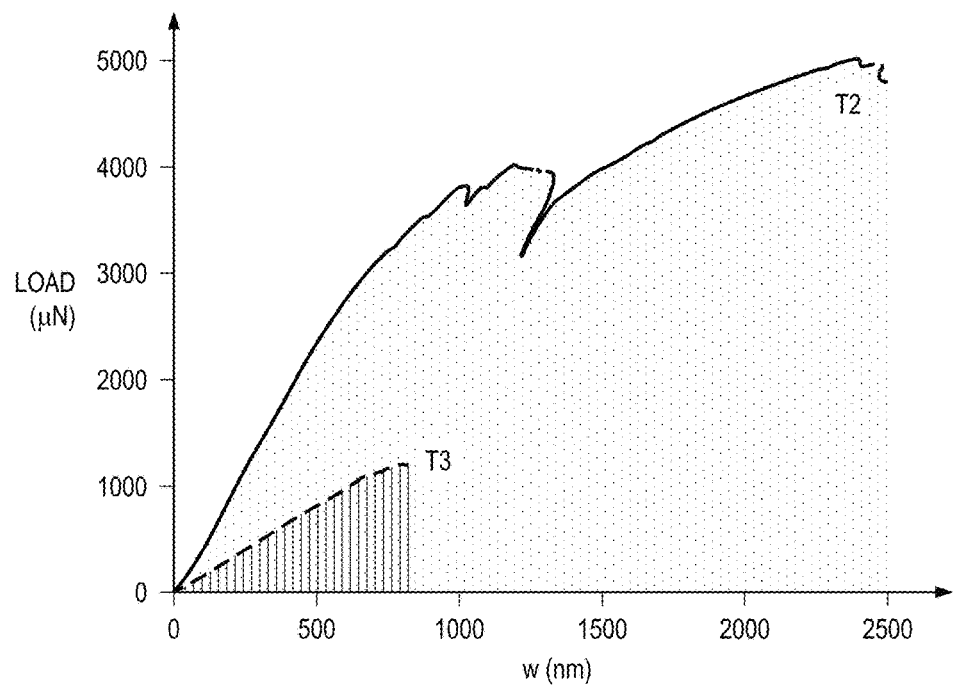

The load-displacement curves captured from loading at the tip of the micro-cantilever beams of equal prismatic dimensions can be compared directly. The areas under their respective force-displacement curves are proportional to the energies required to break the beams in a tensile mode (as shown in FIG. 21A and FIG. 21B). The higher the energy, the lower the fracturability of the rock (more ductile). Higher kerogen content within the beam leads to much larger displacement before failing and thus much higher energy (Energy=work=Force×Displacement).

Elastic Loading in Pre-Yield and Strain Softening in Post Yield

Figure 12B:
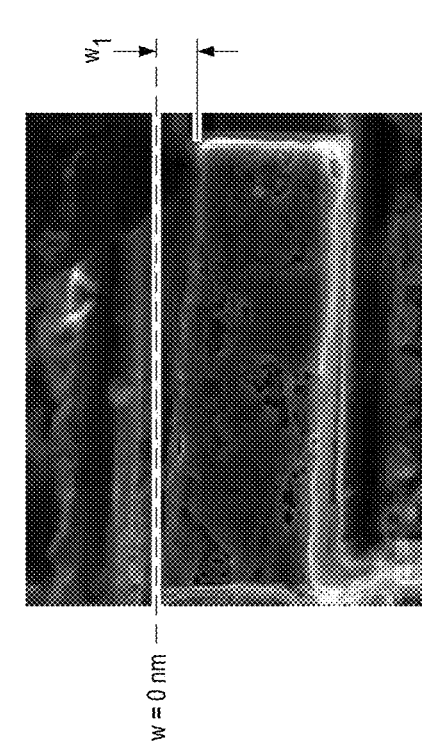
FIGS. 12A-12H show load versus displacement at multiple time instants during progressive cantilever loading of a micro-beam.
Figure 12D:
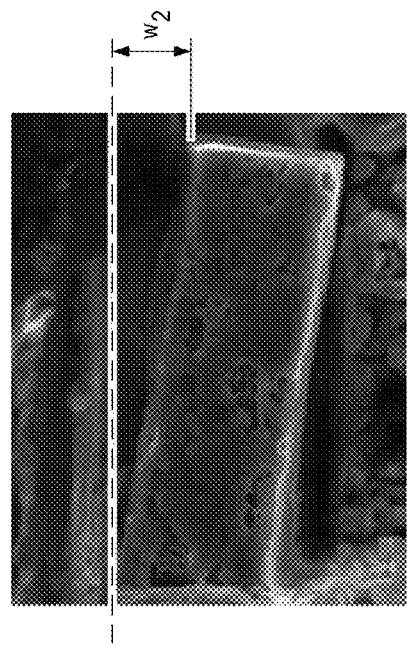
Figure 12A:
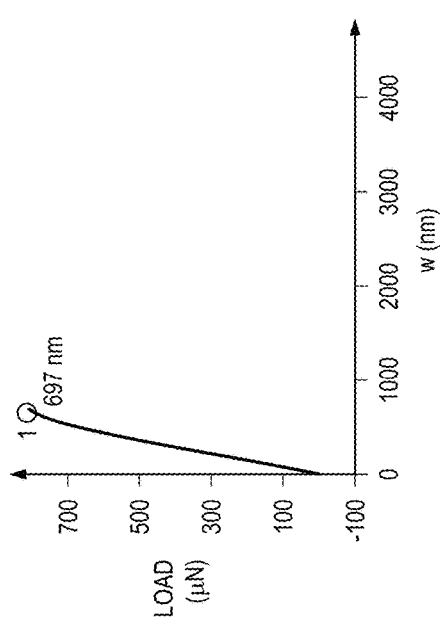
Figure 12C:
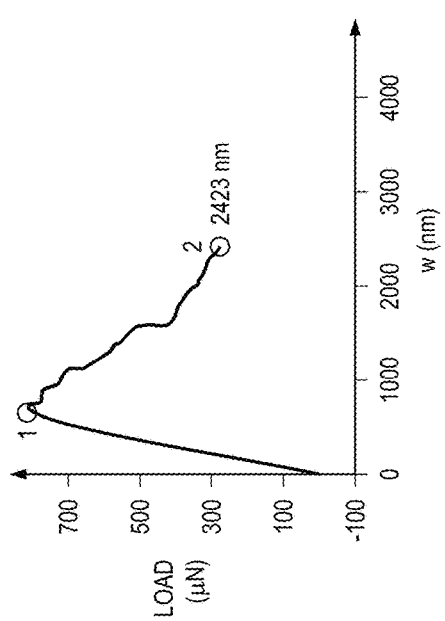
Figure 12E:
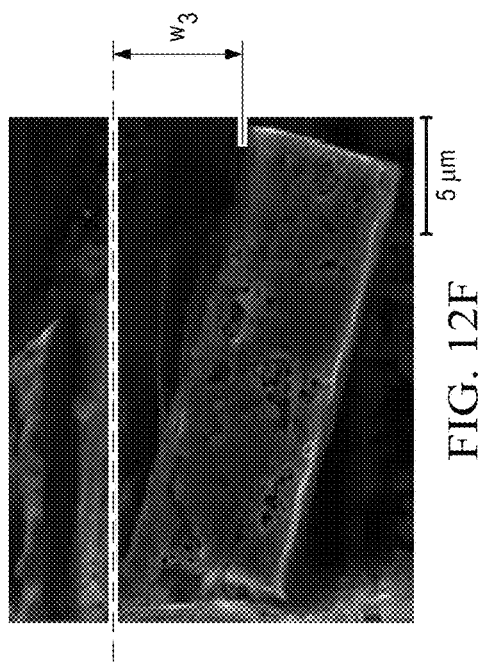
Figure 12F:
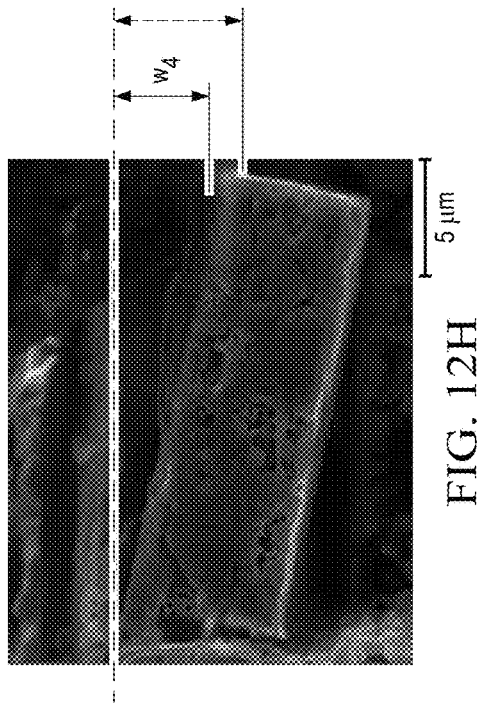
Figure 12G:
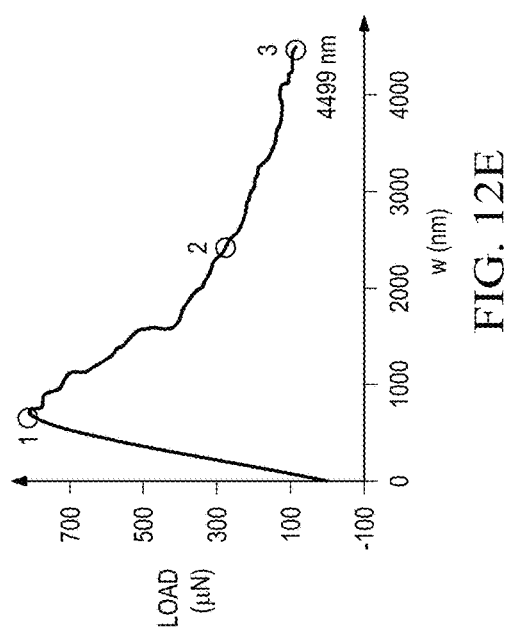
Figure 12H:
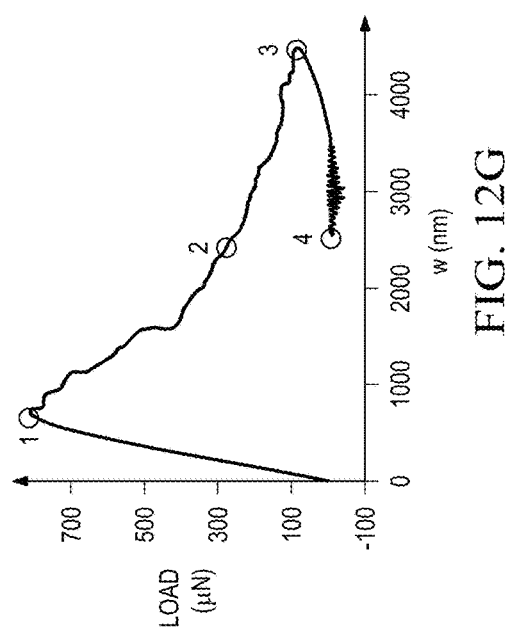

FIGS. 12A-12H show load versus displacement at multiple time instants during progressive cantilever loading of a micro-beam. FIGS. 12A-12H show four stages of a test with the load-displacement correlated to the in situ real-time SEM pictures of the micro-cantilever beam progressive loading to failure. FIG. 12A is a load versus displacement curve showing that a cantilever micro-beam shown in FIG. 12B is continuously loaded up to P=809 μN with a displacement wi=697 nm in a linear elastic load deformation curve. FIG. 12C is a load versus displacement curve that shows that a sudden drop in stress occurs after point 1. FIG. 12D is a SEM image that shows a crack close to the top of the beam. However, the beam continues to deflect and soften as the indenter continuously loads the tip of the micro-beam to point 2 in FIG. 12C. FIG. 12E is a load versus displacement curve and FIG. 12F is a corresponding SEM image of the cantilever micro-beam showing the development of a complex strain softening post yield, and a continuation of fracture propagation towards the bottom of the micro-beam. In this frame, the cantilever micro-beam has totally failed and is almost detached from its support with a maximum deflection, $w_3$=4499 nm. FIG. 12G is a load versus displacement curve and FIG. 12H is a corresponding SEM image of the cantilever micro-beam showing an elastic rebound from point 3 to point 4, and the final deformation when the indenter is lifted. The deflection $w_3$ is greater than $w_4$ as shown by the dotted lines in FIG. 12H and is evidenced by the displacement elastic recovery shown in FIG. 12G relative to FIG. 12E.

Figure 13A:
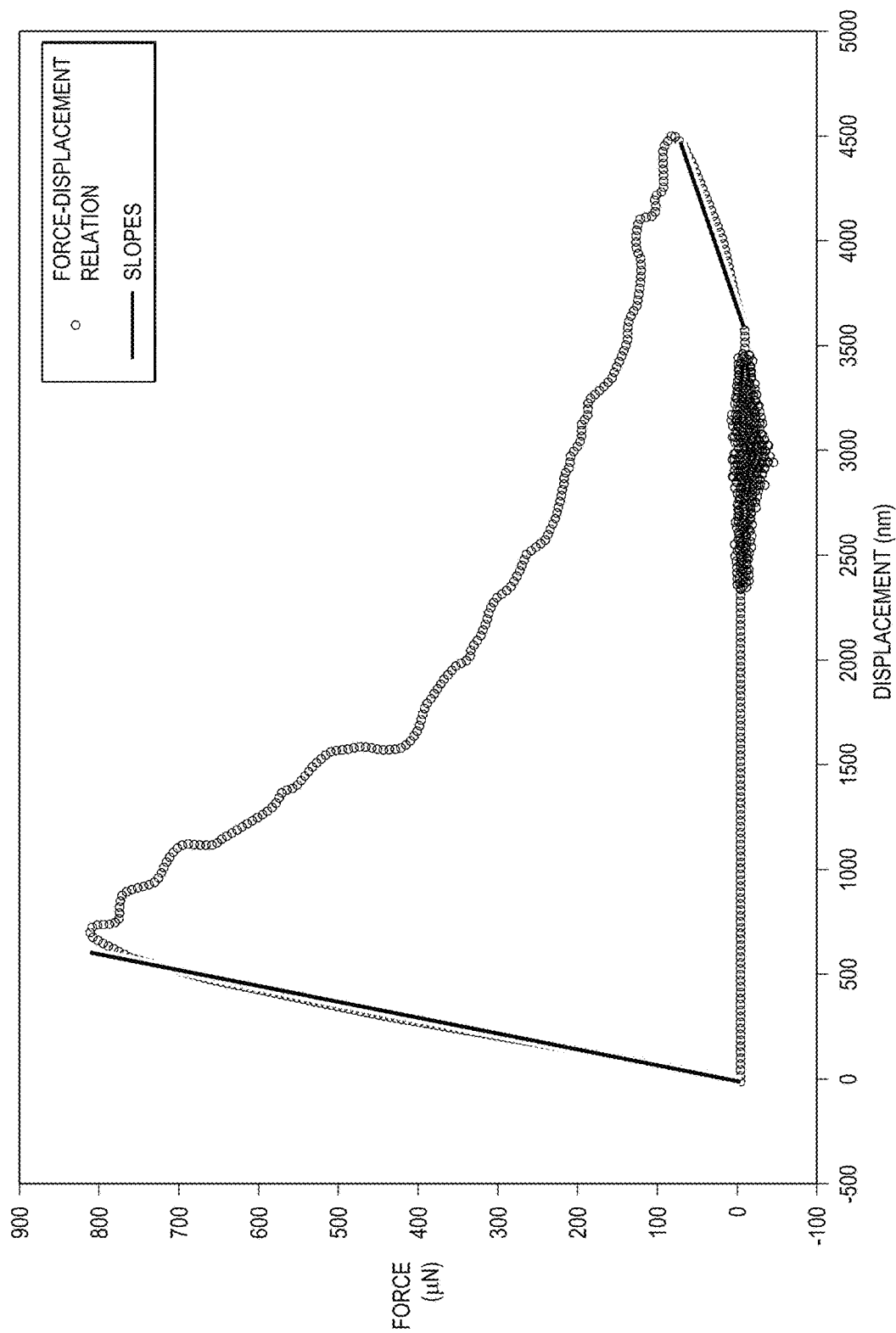

FIGS. 13A and 13B show the plot details with various slopes following failure progress described with reference to FIGS. 12A-12H, particularly FIGS. 12C-12H. FIG. 13B shows the linear elastic load and rebound curves in addition to the step-wise linear strain softening behavior. The linear elastic early performance followed by the various slopes in the strain softening regimes extended the micro-cantilever beam rupture to a very large displacement compared to the 500 nm for the early pure linear elastic deformation. From in-situ visualization, the dashed line represents the first major fracture. In other words, the kerogen, after that point, was supporting most of the load preventing the beam from reaching its rupture strength. The rebound slope at the bottom after stage 3 shows a linear elastic rebound proving that the kerogen cross-linked elastomer did not reach its rupture strength, but rather that mass of kerogen extended the initial shale granular deformation and failure by almost 10 times to 809 µN.

FIG. 14A is an SEM image of a cantilever micro-beam KRS with organic rod-like material. FIG. 14B is a SEM image of Woodford shale. FIG. 14C is a full load-displacement curve. The SEM image in FIG. 14A shows the string-like kerogen. The SEM image in FIG. 14B shows similar worm-like strings of kerogen (dark lines). The SEM image in FIG. 14B is taken with a 40 µm scale while the beam in the SEM image in FIG. 14B has a total length of 22 µm indicating that the polymer-like kerogen can be embedded in the total length of the beam and way further into the micro-cantilever beam fixed support. FIG. 14C shows the full loading history.

Figure 15A:
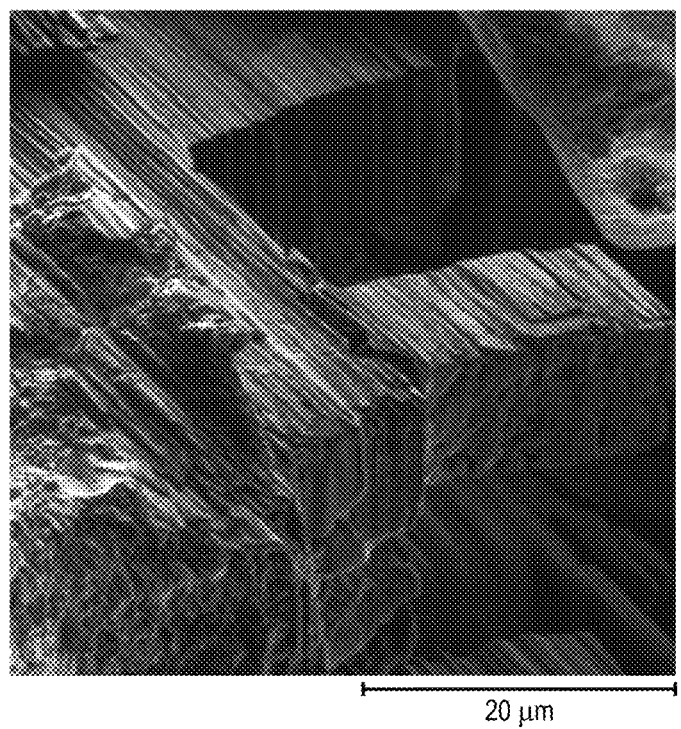
FIGS. 15A and 15B show top views of a cantilever micro-beam with total breakage of the granular shale matrix at the support stage.
Figure 15B:
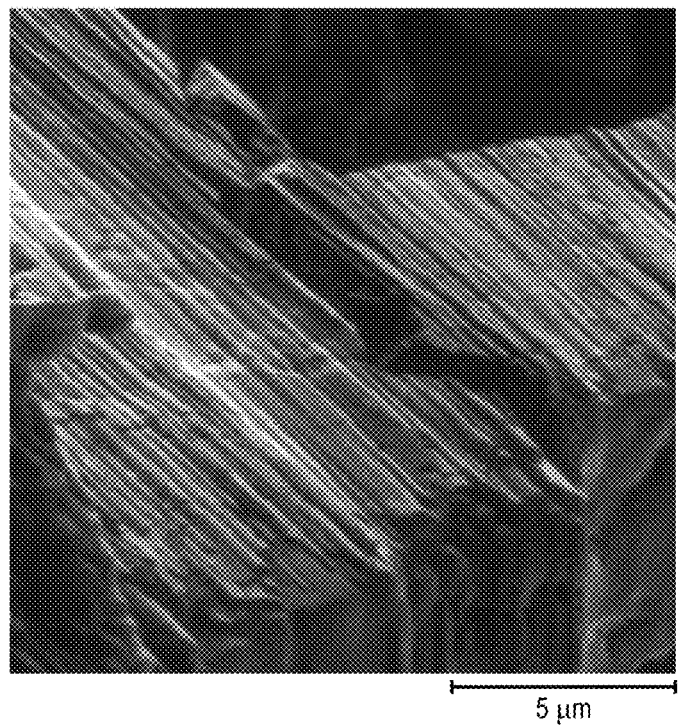

FIGS. 15A and 15B show top views of a cantilever micro-beam with total breakage of the granular shale matrix at the support stage. In contrast to granular material failure, the polymer-like string in the KRS keeps the beam attached to the support after a total tensile failure of the micro-beam. The shale matrix granular failure is clearly broken as shown below in FIGS. 15A and 15B; yet, the micro-cantilever beam is still hanging on after the nano-indenter load was released. This behavior is typical of composite beams such as reinforced concrete beam, or in geo-grid reinforced site constructions. Post failure analysis shows strain softening behavior that can be reproduced using numerical simulation. Since the organic content in these shales, such as kerogen, was never observed in tensile loading or tensile failure to have any effects, the constitutive model for mechanical behavior of the kerogen matrix intertwined with other shale minerals is nonexistent. A two dimensional numerical model mimicking the micro-beam response in this one test was constructed as described below. This is an attempt to explore the potential constitutive model for the micro-cantilever beam mechanical behavior through matching the force-displacement curve by placing a percent of volume of organic matter with sustainable tensile strength characteristics at the support.

Numerical Modeling of Cantilever Micro-Beam Behavior

Figure 16A:
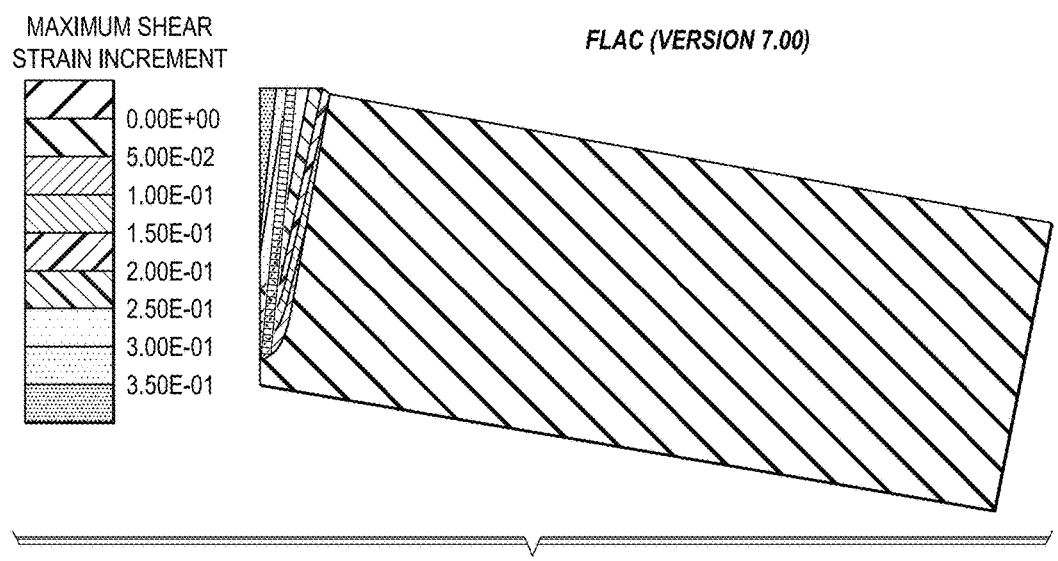
FIGS. 16A-16D show a numerical modeling of a cantilever micro-beam behavior.
Figure 16B:
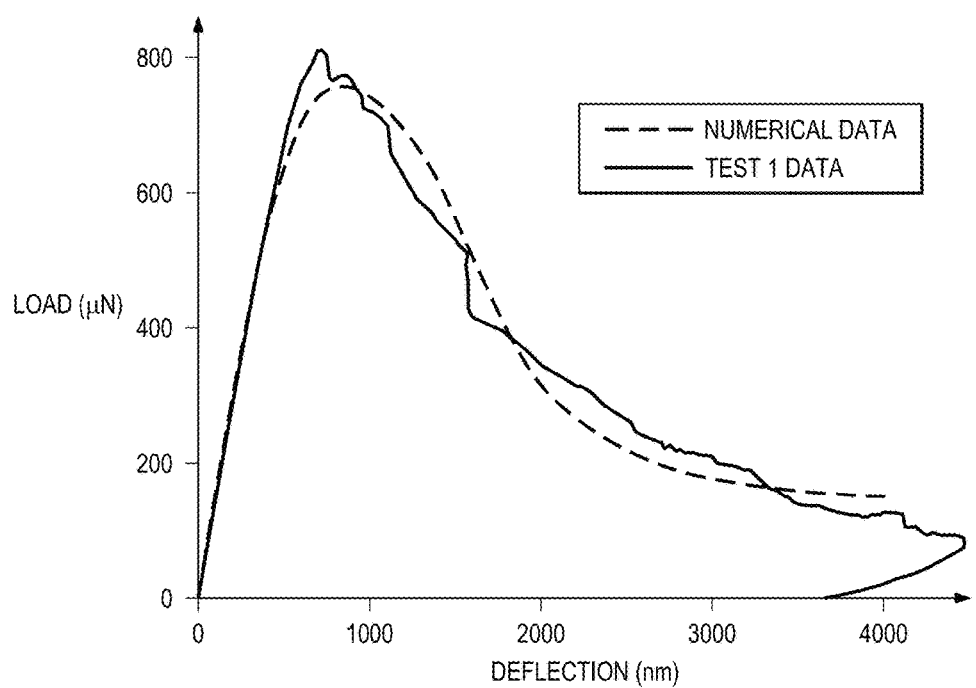
Figure 16C:
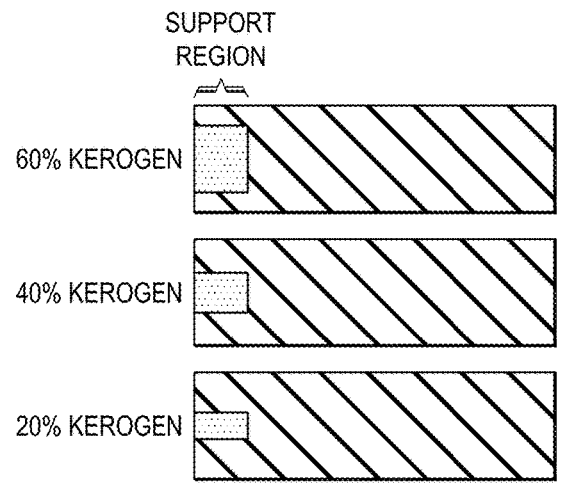
Figure 16D:
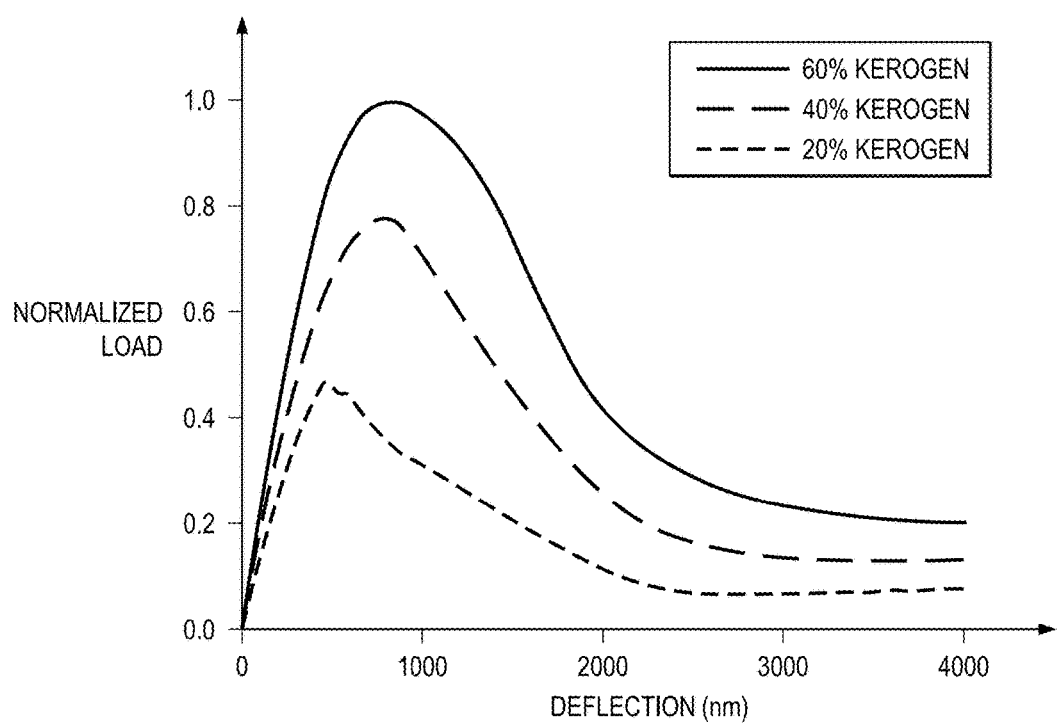

FIGS. 16A-16D show a numerical modeling of a cantilever micro-beam behavior. FIG. 16A shows the contour of maximum shear strain with tensile yielding indicator. FIG. 16B shows the comparison of force-deflection curve measured by experiments and numerical modeling. FIG. 16C shows three simulation cases with kerogen content varying from 60% to 20%. FIG. 16D shows normalized force-deflection curves from three cases also illustrating the modulus of toughness variation. SEM images indicate that the kerogen content is quite rich at the fixed end in Test 1 and thus contribute to the bending and the mechanical response of the micro-cantilever. In this initial plane-stress numerical model, the real geometry of the micro-cantilever beam is used, for example, 21.69 µm in length and 8.80 µm in thickness. The out-of-plane direction is unity (1 µm), but the loading force monitored in the numerical model is scaled by 9.49 to account for the thickness of the micro-cantilever beam in the nano-indentation test.

It is observed that the tensile yielding only took place at the fixed end. To simplify the setup in the numerical model, the left column of elements ("kerogen") is assigned with strain softening capability while the rest of the elements are assumed to be pure elastic material. In the numerical model shown in FIG. 16A, the left boundary of the model is fixed in both X- and Y-directions. The grid point at the upper right corner is loaded in the downward direction at a constant rate of $1\times10^{-5}$ µm/step. The reaction force and deflection at the loaded grid point are monitored during the entire course of the simulation. The modeling approach is to adjust material properties so that the force—deflection curve measured in the numerical simulation matches with the measurement in experiment described with reference to FIGS. 12A-12H. The elastic response (before the peak) is matched by adjusting material stiffness in the model. The plastic component is matched by adjusting the strain softening curve of the kerogen material. Simulation indicated that a Young's modulus of 14 GPa in tension and a bilinear tensile strain softening (for example, tensile strength is 130 MPa initially, decreases to 85 MPa at plastic tensile strain of 17% and further drops to the residual tensile strength of 12 MPa at plastic tensile strain of 70%) seem to give quite a good match, as presented in FIG. 16B. The tensile crack area developed near the fixed end in FIG. 16A also looks similar to the lab observation. The Young's modulus used in the numerical model is very close to the values measured for the four micro-beams.

Strain Hardening Before a Sharp Snap at Failure

Figure 17:
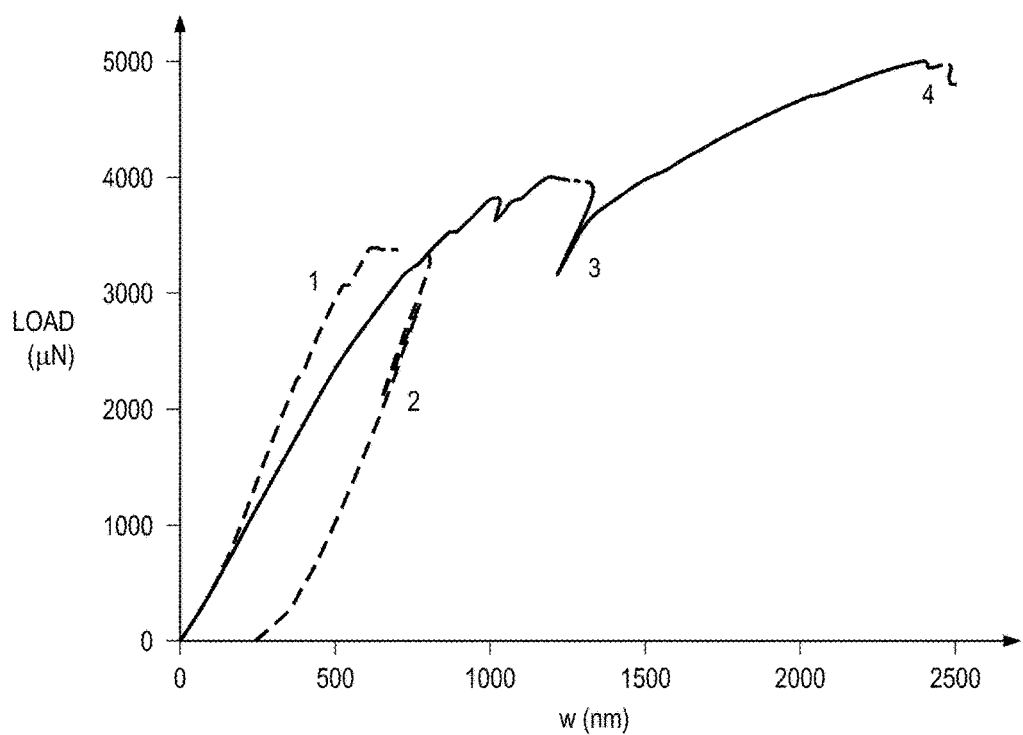
FIG. 17 is a load versus displacement curve showing strain hardening before a sharp snap at failure.
Figure 18A:
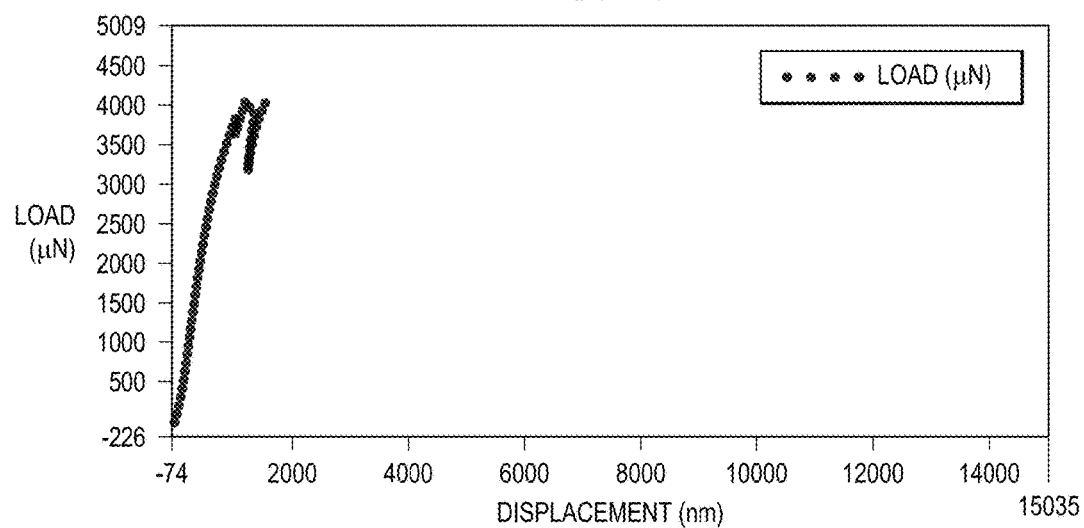
FIGS. 18A-18F show load versus displacement progress between two points.
Figure 18B:
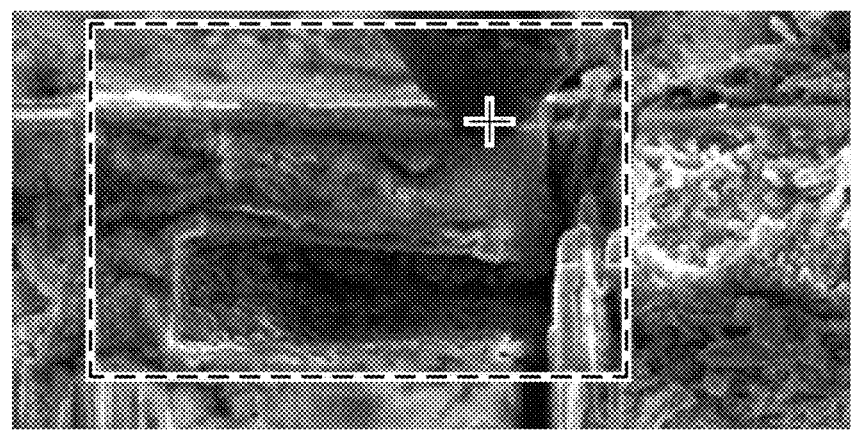
Figure 18C:
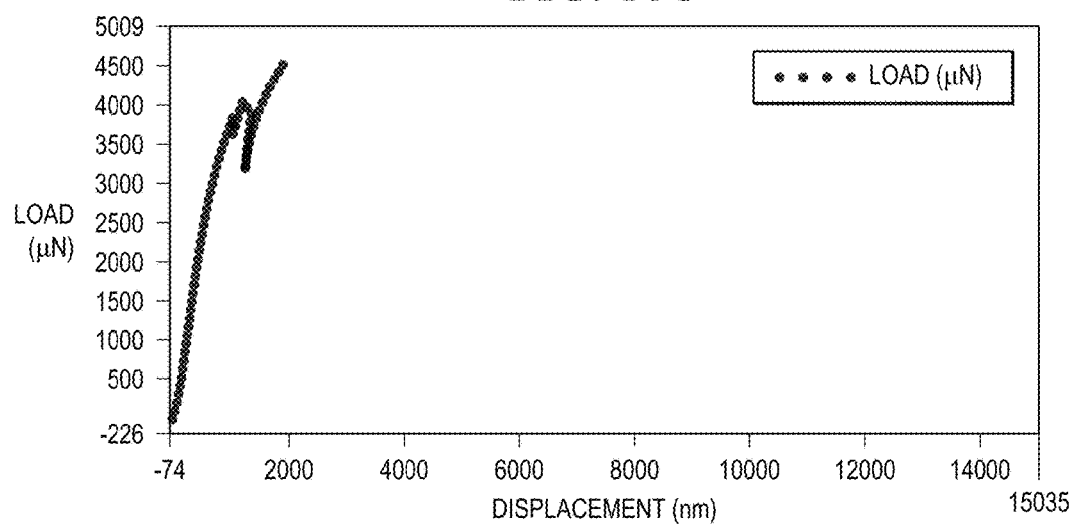
Figure 18D:
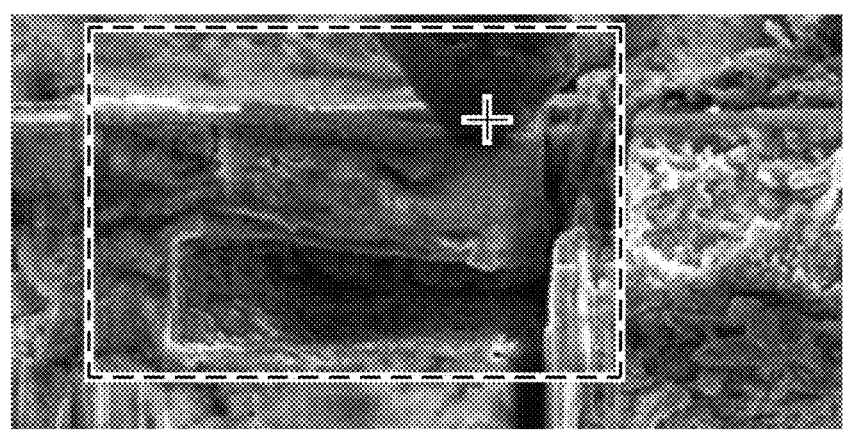
Figure 18E:
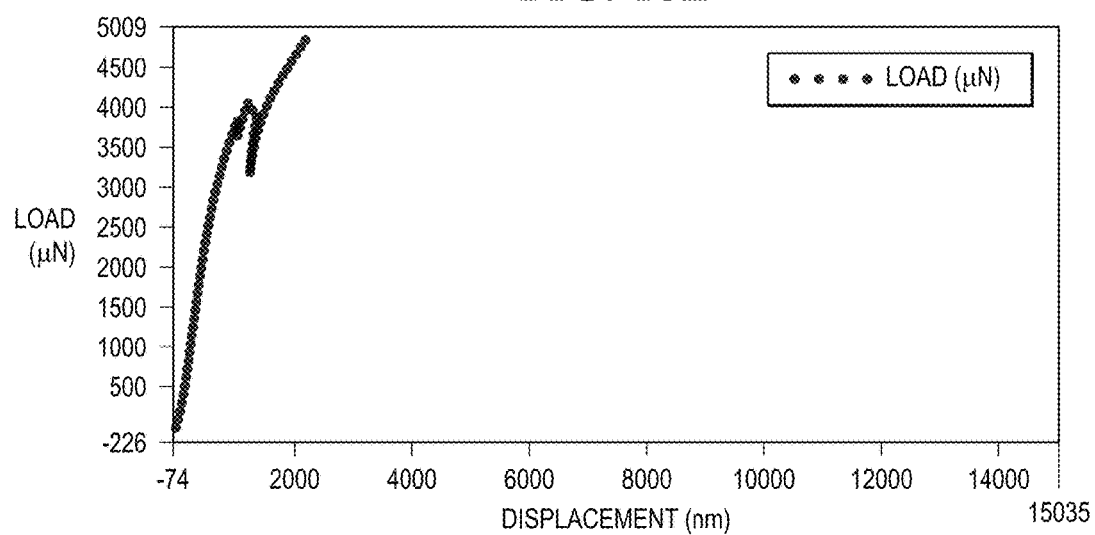
Figure 18F:
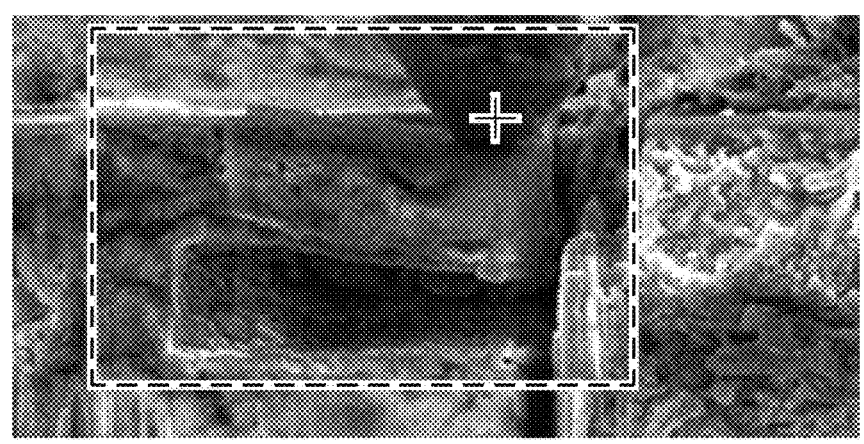

FIG. 17 is a load versus displacement curve showing strain hardening before a sharp snap at failure. The test described with reference to FIG. 17 was performed in two stages. The first stage showed load/unload highlighting relatively elastic behavior with one minor kink observed at 3000 µN. But, the micro-beam continued displaying elastic behavior during loading up to 3500 µN. The beam was then unloaded, stopping at point 2 then loading and unloading again to confirm its elastic linear behavior. An approximately equal parallel slope to the first loading curve and an almost total recovery of the elastic linear displacement was obtained.

FIG. 17 also shows the second stage, where the same micro-beam was immediately reloaded without any disturbance in between stages or even any lapse of time. The progress of this loading is illustrated in FIGS. 18A-18F (frames 1-4 in chronological order). As shown in FIGS. 18A-18F, the fracture has already propagated as the load increased from 3500 to 4000 µN across the depth, h, of the micro-beam near the fixed support yet the load continue to increase reaching above 5000 µN before total rupture. Passing the threshold of the earlier elastic, a kink is suddenly observed at 3800 µN, and a minute transversal crack shows up on the beam. Then, the micro-beam recovered shortly to a load value close to 4050 µN before a substantial failure shown in FIG. 18F (Frame 3) thus decreasing the load to a little less than 3000 µN shown on FIG. 17 as point 3. As the loading continues beyond this point, clear strain hardening behavior is observed, while a major fracture has developed as seen in FIG. 17 (Frame 4). However, the micro-beam continues to gain energy before the final snap and total failure at point 4 in FIG. 17. This ultimate tensile load is equivalent to the ultimate tensile stress (UTS) which is a value that carries much significance in our geomechanics source shale field fracking applications. In fact, the UTS is much more important than the UCS since hydraulic fracturing is a tensile mode one crack failure and not a compressive one.

Brittle Failures with Minimal or No Yield

Figure 19A:
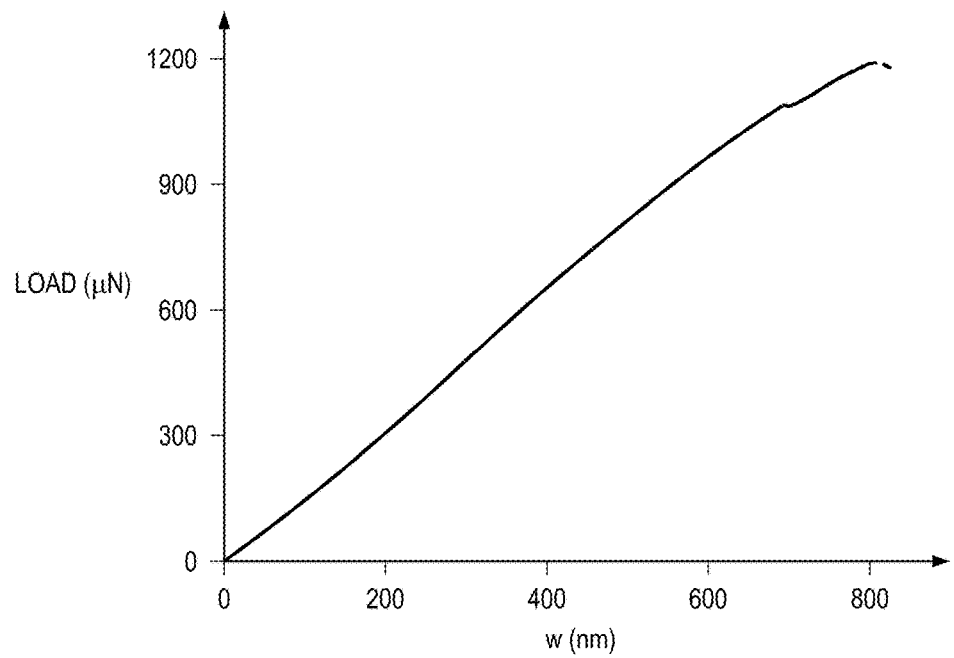
FIGS. 19A and 19B are two load versus displacement plots of micro-cantilever beam tests.
Figure 19B:
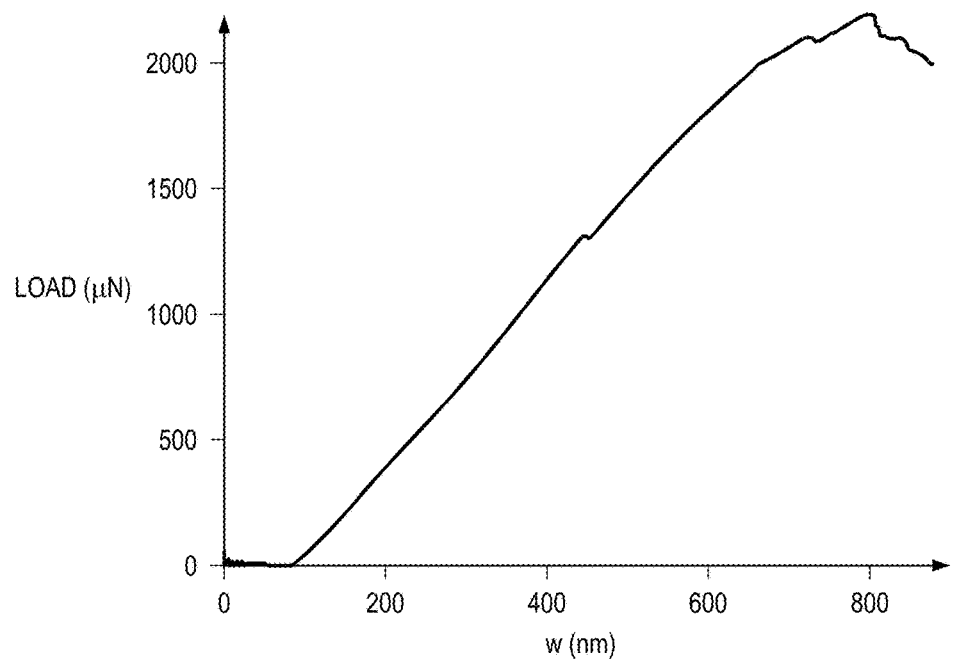
Figure 20A:
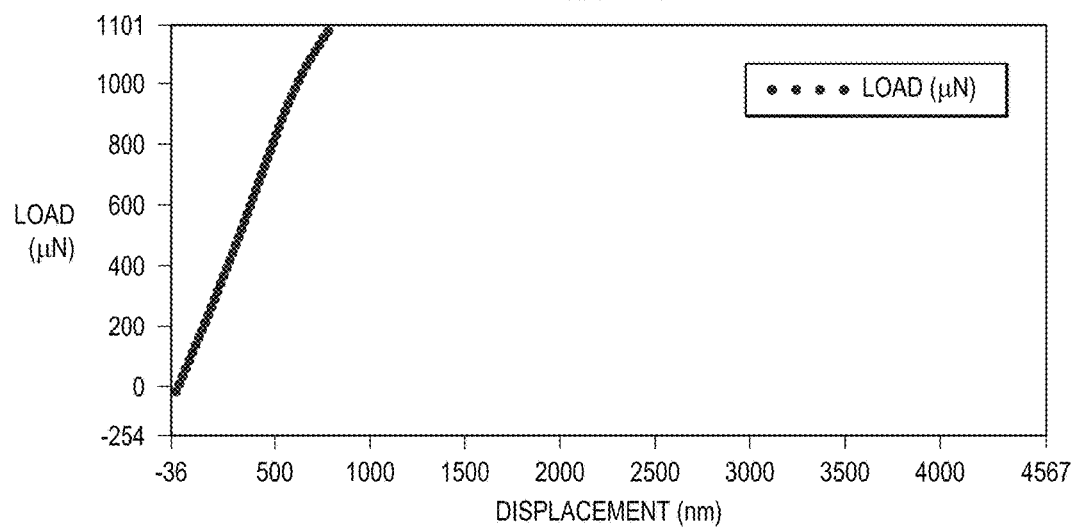
FIGS. 20A-20D show load versus displacement curves and SEM images before and after brittle failure of a sample.
Figure 20B:
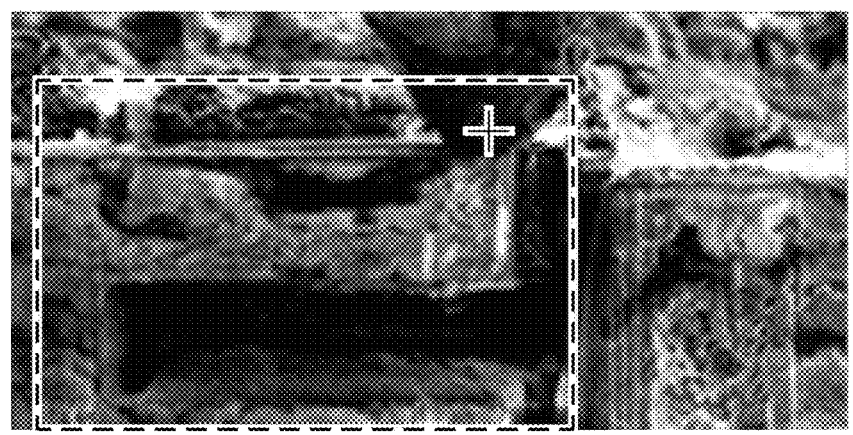
Figure 20C:
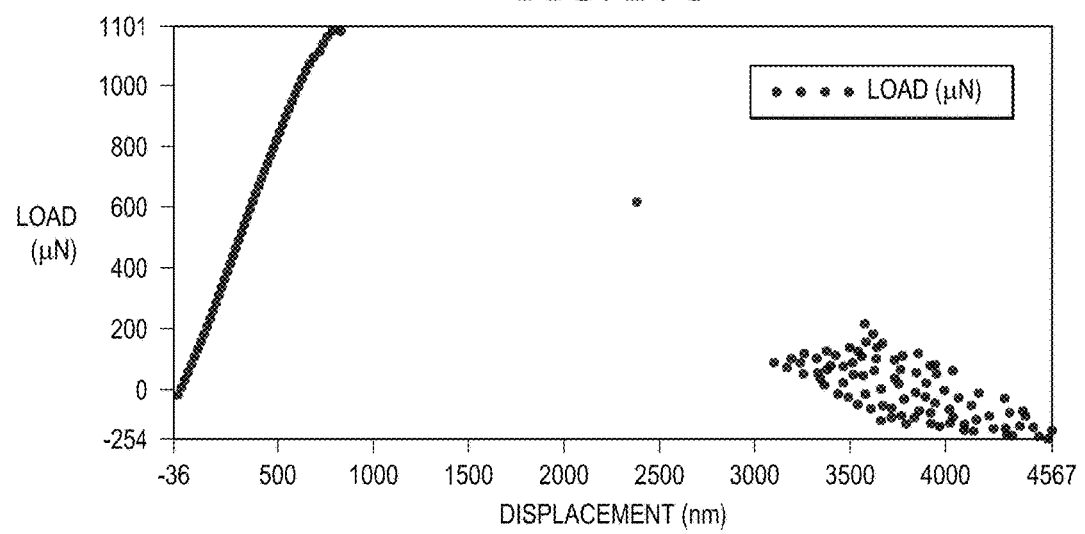
Figure 20D:
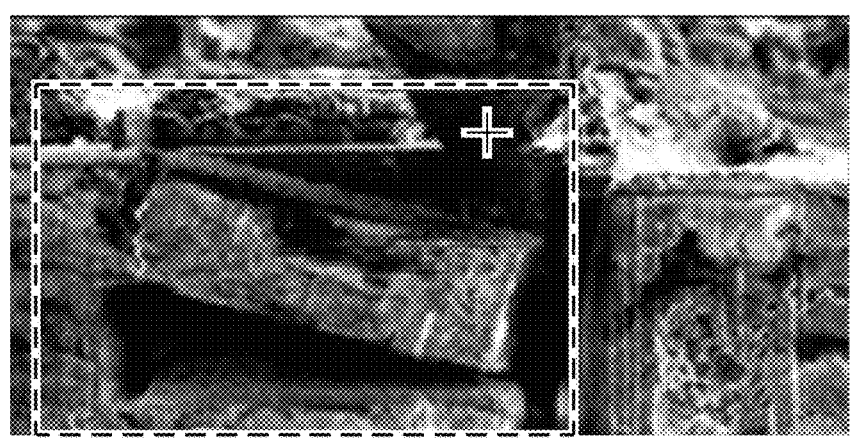

FIGS. 19A and 19B are two load versus displacement plots of micro-cantilever beam tests. FIGS. 20A-20D show load versus displacement curves and SEM images before and after brittle failure of a sample. Micro-cantilever beams T3 and T4 are shown in FIGS. 19A and 19B, respectively, where sharp brittle failures with clear snaps were observed during the in situ SEM imaging. The brittle failure is indicative that there are only trace amounts of organic matter at the fixed support of the micro-cantilever beam. As defined early on, "trace" organic matter is an amount that is not enough to alter the mechanical behavior. This fact was illustrated in the numerical simulation described above, where reducing the volumetric percentage of kerogen at the support diminished the strain softening as well as the ultimate load observed during elastic loading. The Young's moduli measured at 50% of the maximum load in the elastic regime are very close in value, as shown in Table 3 (below); yet their failure loads varied by almost 100%.

TABLE 3

The summary of dimensions and calculated values for each of the micro-beam tests.

| Test | L (μm) | b (μm) | h (μm) | I (μm$^4$) | P (μN) | E (GPa) |
|---|---|---|---|---|---|---|
| 1 | 21.69 | 9.49 | 8.80 | 539 | 290 | 9.1 |
| 2 | 21.37 | 7.36 | 9.23 | 483 | 1016 | 30.4 |
| 3 | 24.12 | 7.25 | 9.47 | 514 | 353 | 14.2 |
| 4 | 23.18 | 7.95 | 9.94 | 651 | 478 | 13.5 |

In summary, the four micro-beams showed very interesting behaviors within a span of 200 μm in the preserved Woodford KRS. In Table 3, the dimensions of each micro-cantilever beam are summarized to illustrate the difficulty of attempting to obtain exact dimensions for each milled porous micro-beam. The calculated values of the Young's Moduli were taken at ~50% from the linear elastic loading span, that is, they were calculated based on picking up the corresponding load, P, and the deflection, w, at 50% on the four loading curves.

FIGS. 21A and 21B show moduli of ruptures of granular shale (T3) compared to kerogen elastomer cross-linked polymer in T1 and T2. The modulus of toughness as the work/energy needed before the total rupture of the beam is illustrated in FIGS. 21A and 21B. It can be seen that the two shaded areas where T3 required ~10% of the toughness needed to break micro-beam T2. A similar comparison can be made between T3 and T1 although the magnitude is different. Hydraulic fracturing involves the tensile cracking of this composite KRS formation.

Micro-Pillar Compression Testing

Figure 22A:
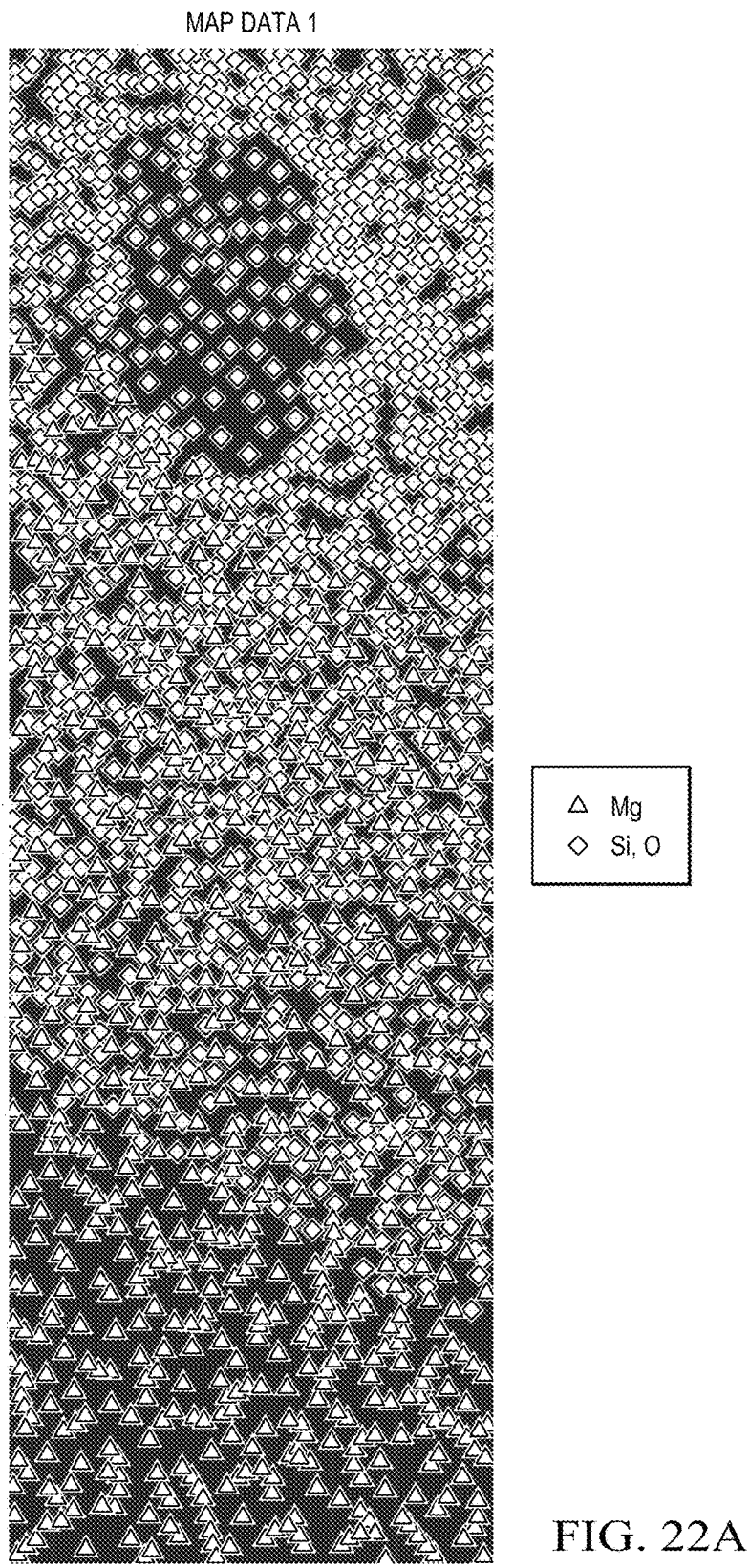
FIG. 22A is a SEM image of a micro-pillar pre-loading overlaid with energy dispersive X-ray spectroscopy (EDS) map.
Figure 22B:
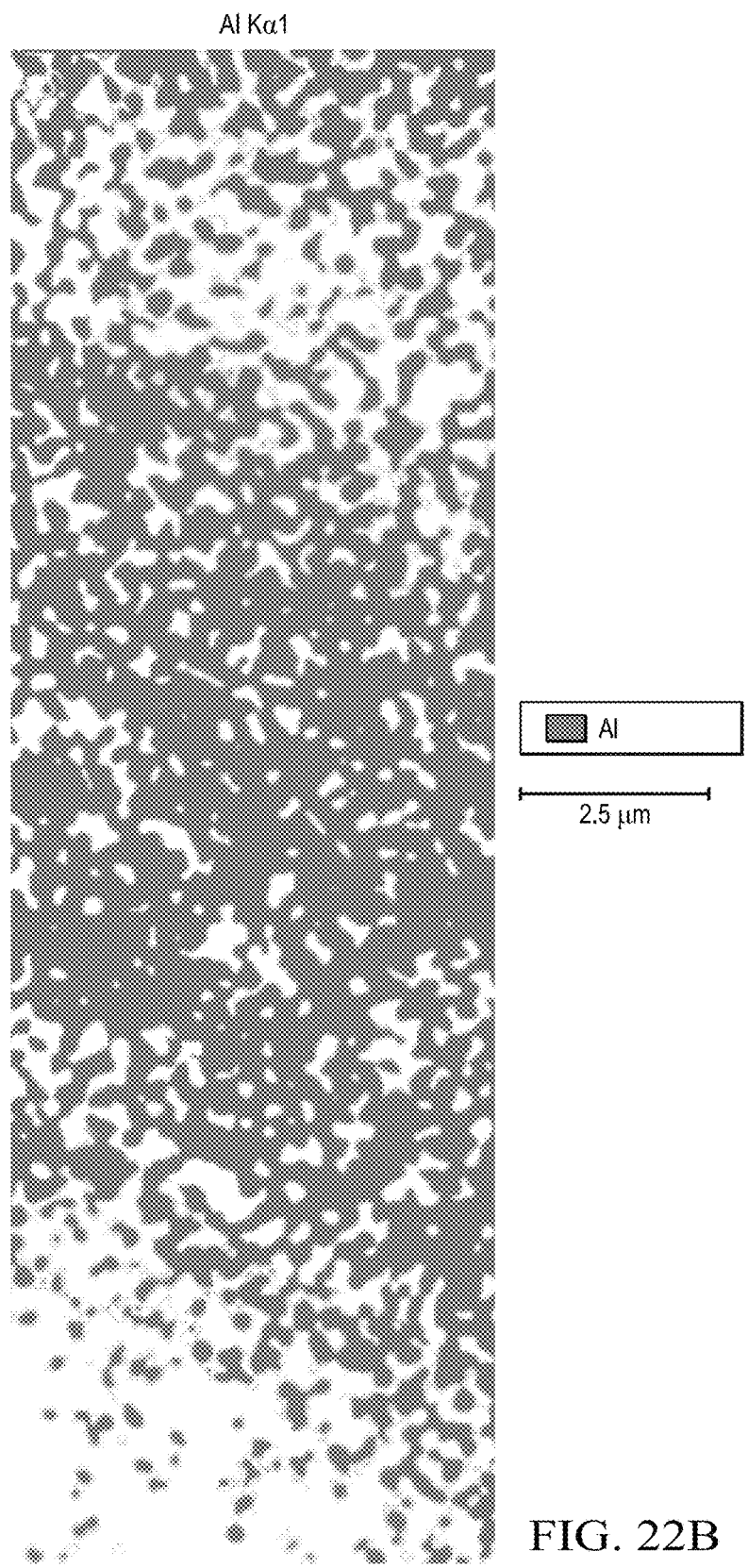
FIG. 22B is the EDS of the micro-pillar displayed and superimposed.

FIG. 22A is a SEM image of a micro-pillar pre-loading overlaid with EDS map. FIG. 22B is the EDS of the micro-pillar displayed and superimposed. While three micro-pillars were prepared for the testing only one ended up being loaded to failure. EDS has been used to analyze nano-indentation results and to isolate mechanical phases when describing Woodford mechanical behavior. In this test, EDS was also conducted on the micro-pillar face before testing as shown in FIG. 22A. A pre-existing inclined shear band can be observed across the center of the micro-pillar, as evidenced by the orange color which is enlarged in the superimposed frame shown in FIG. 22B. The top of the pillar has a high concentration of silicon and oxygen, indicating silica, the middle band contains aluminum, silicon, potassium, and oxygen indicating clay, while the bottom section has a high concentration of calcium and magnesium indicating dolomite.

Figure 23A:
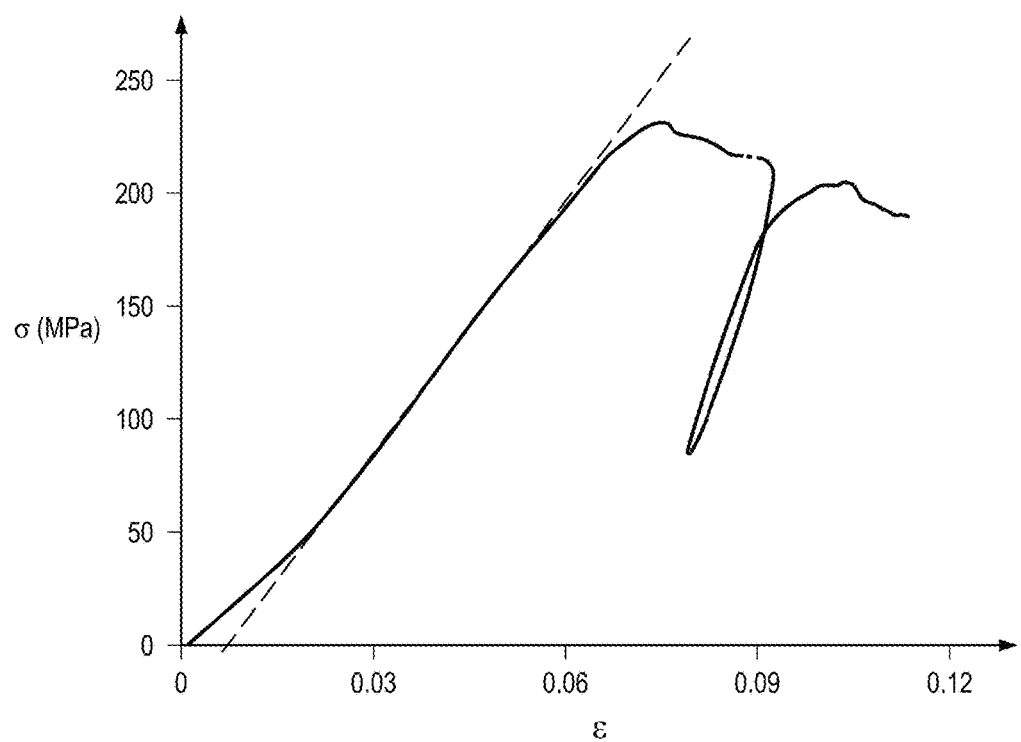
FIG. 23A is a plot of stress versus strain in a micro-pillar compression test.
Figure 23B:
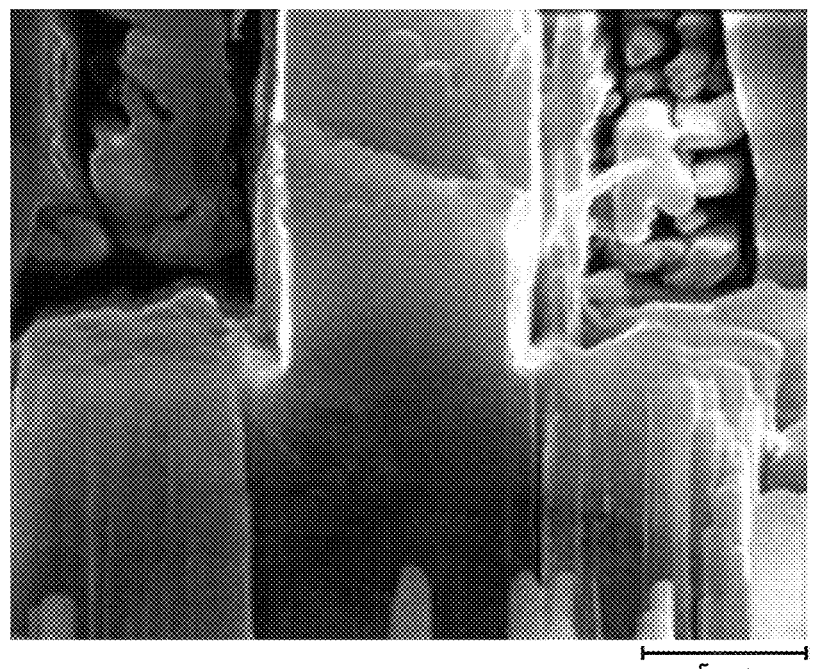
FIG. 23B is a SEM image of the micro-pillar after failure.
Figure 23C:
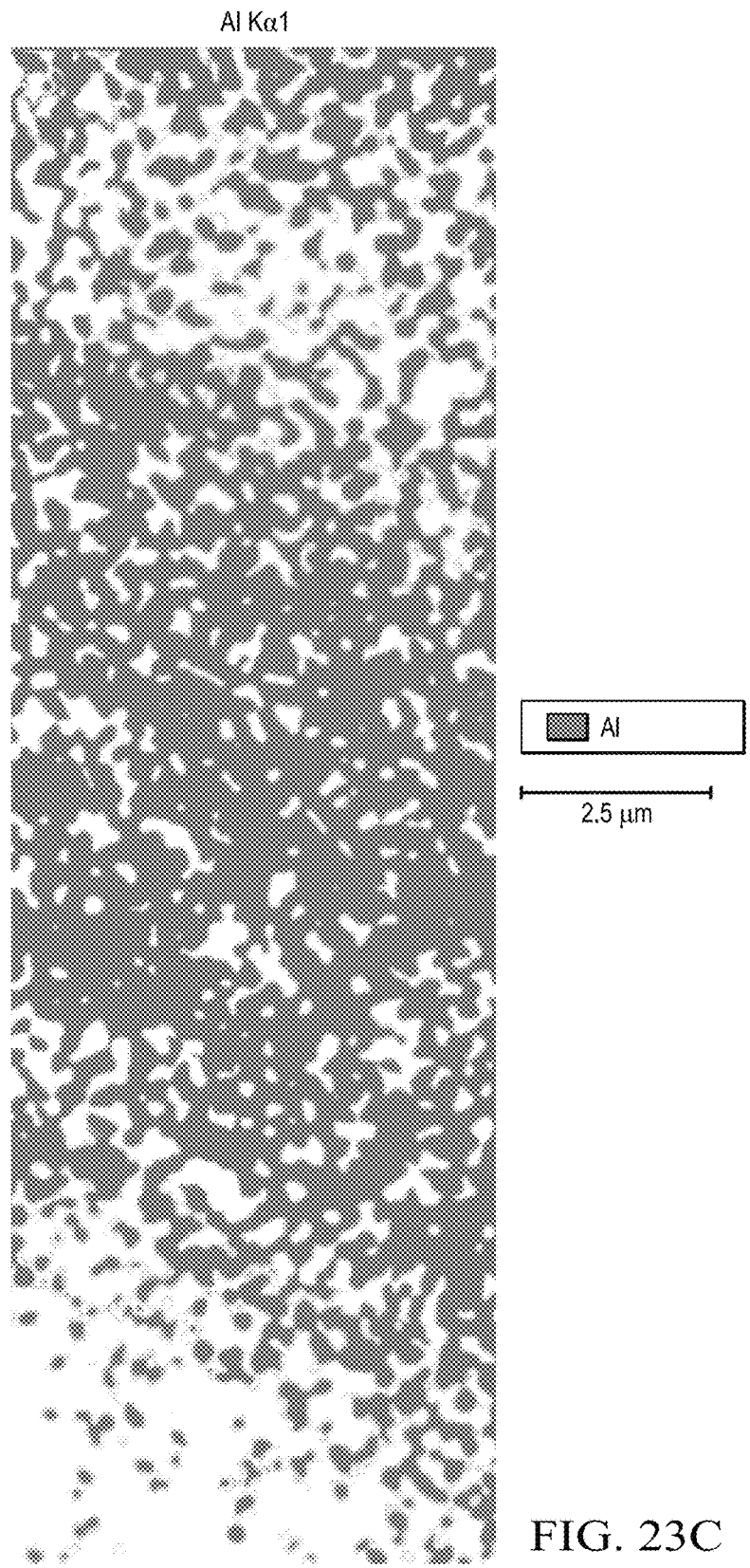
FIG. 23C is an EDS map of the micro-pillar superimposed showing the intact shear band plane pre-failure.

FIG. 23A is a plot of stress versus strain in a micro-pillar compression test. FIG. 23B is a SEM image of the micro-pillar after failure. FIG. 23C is a EDS map of the micro-pillar superimposed showing the intact shear band plane pre-failure. The result in FIG. 23A shows the various stages of the stress-strain curve. Initially, a non-linear loading section is observed. Then, as the load increases in a linear elastic part, illustrated on the plot with the straight line extension, before the micro-pillar goes into short yield. Then, a load-unload section and eventually failure are observed. This stress strain curve resembles exactly, in its stages, the uniaxial 2"×4" Woodford KRS sample described above. Even the load and unload part of the curve, shows a higher Young's modulus, also consistent with the load/unload cycles described above. Since the loading/unloading occurred after a short yield, the much higher Young's modulus could be due to permanent micro-pillar consolidation or pore/grain compaction. Eventually, the shear band acted as a weak plane along which the micro-pillar sheared during failure shown in FIG. 23B with the superimposed pre-failure EDS map in FIG. 23C. Shear bands often form when granular materials undergo ductile behavior under a given loading configurations. Having this pre-existing condition, the shear failure showed little interference of the kerogen polymer-like behavior.

The micro-beam in T1 exhibited ductile behavior as shown earlier, and it post-yielded in a strain softening regime while the ductile behavior of Test 2 demonstrated strain hardening in post-yield. Meanwhile, the micro-beams in Tests 3 and 4 exhibited brittle failure modes. Determining the reasons for the differences between each of the failed micro-beams is important to be able to upscale and convert this understanding into predictive tools, when it comes to hydraulic fracturing, wellbore drilling, reservoir optimal productivity, and many other oil and gas field applications.

Figure 24A:
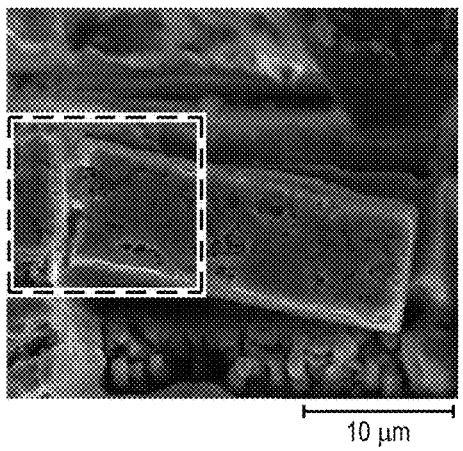
FIGS. 24A-24F are SEM images of failed micro-beams.
Figure 24B:
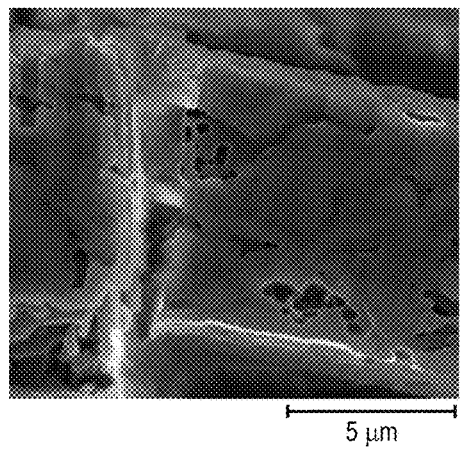
Figure 24C:
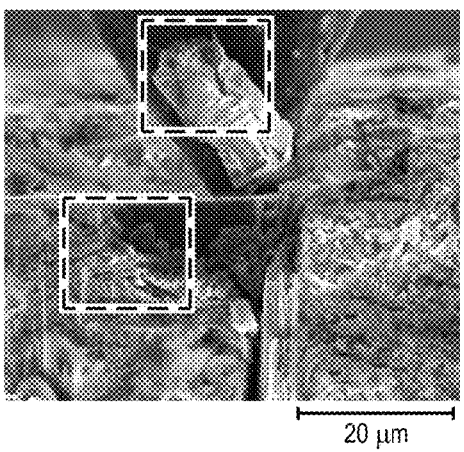
Figure 24D:
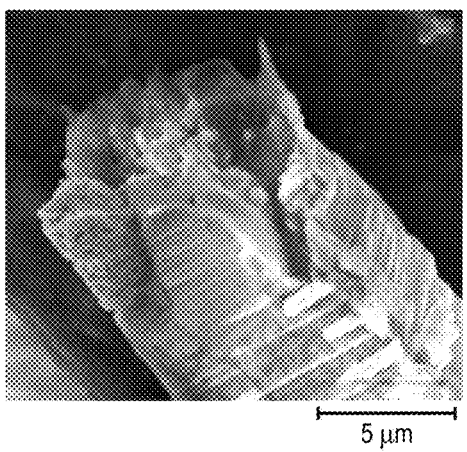
Figure 24E:
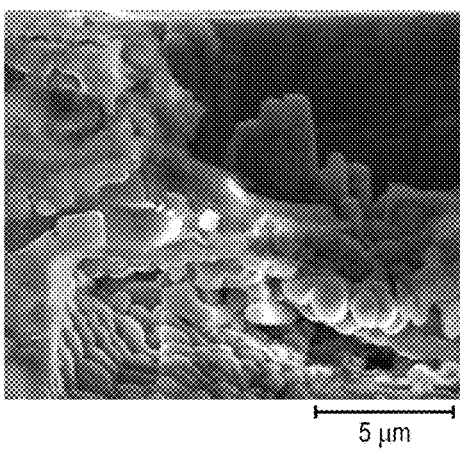
Figure 24F:
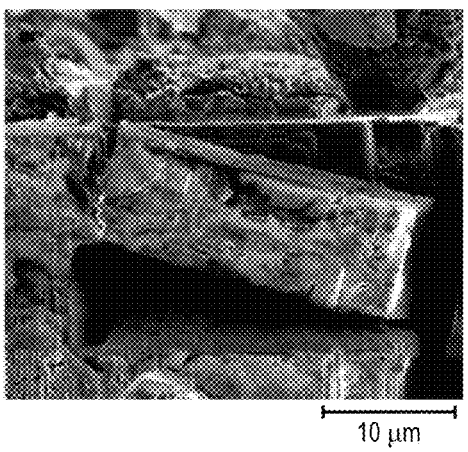

FIGS. 24A-24F are SEM images of failed micro-beams. The squares in FIGS. 24A and 24C indicate sections expanded in subsequent frames and in FIG. 24F. The role of kerogen and other organic matter as cross-linked polymer contributing substantial tensile strength to the shale micro-beam have been observed in the KRS tensile loading experiments. In T1, the beam granular structured totally failed, and yet the kerogen string rebounded the whole beam back recovering some of it elastic energy. FIGS. 24A and 24B show that the beam had separated from its support; and yet, the tensile elastic string stretched but did not rupture or pull out, but rather was still fully embedded in the beam. In other words, the kerogen string never reached its full "modulus of toughness" or total energy needed for rupture while early on in the loading range the granular part of the beam reached its "modulus of toughness" in tensile loading. The amount of kerogen at the support was enough to give it the strain softening behavior where the micro-beam acted as a composite material such as reinforced concrete beams.

In T2, the amount of kerogen was way too high and even overwhelming at the support with little volume of the clay or non-clay granular material. The volume of the organic matter that stayed behind at the support is evident by the large cavity left on the micro-beam after total collapse shown in FIGS. 24C and 24D. The volume of the kerogen was large enough and stiff enough to carry the micro-beam into a strain hardening post yield type of failure with a huge modulus of toughness contributing to the overall shale micro-beam behavior. The progress of failure in T2 reinforced our early hypothesis that the cross-linked polymer nature of kerogen and its intertwined structure with the non-clay and clay mineral matrix is the one holding the granular shale matrix together resulting in large and unexpected values for granular material in tensile failures. Also, the fracture has totally developed across the depth of the beam, yet the beam continued taking more load and exhibiting strain hardening until total failure.

This work sheds new light on the composite nature of kerogen-rich shale. It showed that the composite nature of the organic rich shale has tensile strength characteristics that are relevant. An obvious question is, "why for the past decade or so in rock mechanics testing we did not pick up on the tensile attributes of this KRS shale or any other source rock formation?" The answer is simply that these tensile characteristics of polymers are easily masked in the ISRM standard testing methods for macroscale geo-mechanics material characterization such as the Brazilian test and other approved tensile strength measurements for rocks. These tests were never designed to isolate or measure the tensile strength of polymers. This natural cross-linked polymer component, kerogen, with its tensile characteristics was not known previously to contribute to the tensile strength of any known rock loaded in tension. Now that the organic rich source shale formations are loaded under tensile forces, for example. Mode One crack opening and crack propagation, the UTS of the organic components is of paramount importance to successfully engineer our lab and field applications Example of a Hydraulic Fracture Treatment Process The experiments discussed prior can yield valuable data. For example, the fracturability of mudstone can be predicted by interpreting the load curves from varying samples. The fracturability data assists in calculated pressure in flow rates during a hydraulic fracture treatment process, such as the example illustrated later. The experiments discussed prior can also be utilized for evaluating different chemical treatments. For example, a shale sample can be treated with a fluid designed to break-down kerogen. The treated sample can then be fabricated into a micro-beam and tested to demonstrate the fluids effects on kerogen. Such knowledge can improve the effectiveness of hydraulic fracture treatments such as the example given in the following paragraphs.

The kerogen content of different beam specimens in the previously discussed experiments can be varied and the tensile test results compared directly. The beam specimen can even come from the same bulk shale sample, but taken from high, low, or intermediate kerogen content regions. Without the kerogen, the beam will undergo brittle tensile failure under load, with minimal tensile mode energy required to break it. With kerogen, the energy required as well as its correlative tensile strength will be much higher.

In compression, higher kerogen content will lead to lower compressive strength. Therefore two pillars of equivalent size and dimension but different kerogen content will yield differently under compressive loads. Kerogen is understood to be at least 10 s time weaker than the rock granular structure, depending on its maturity, in compression. Hydraulic fracturing is primarily a tensile failure of the rock in a Mode I fracture propagation criteria, so the tensile properties (micro-cantilever beam tests) are the most relevant to fracturability considerations when it comes to optimizing hydraulic fracturing planning and execution.

Figure 25:
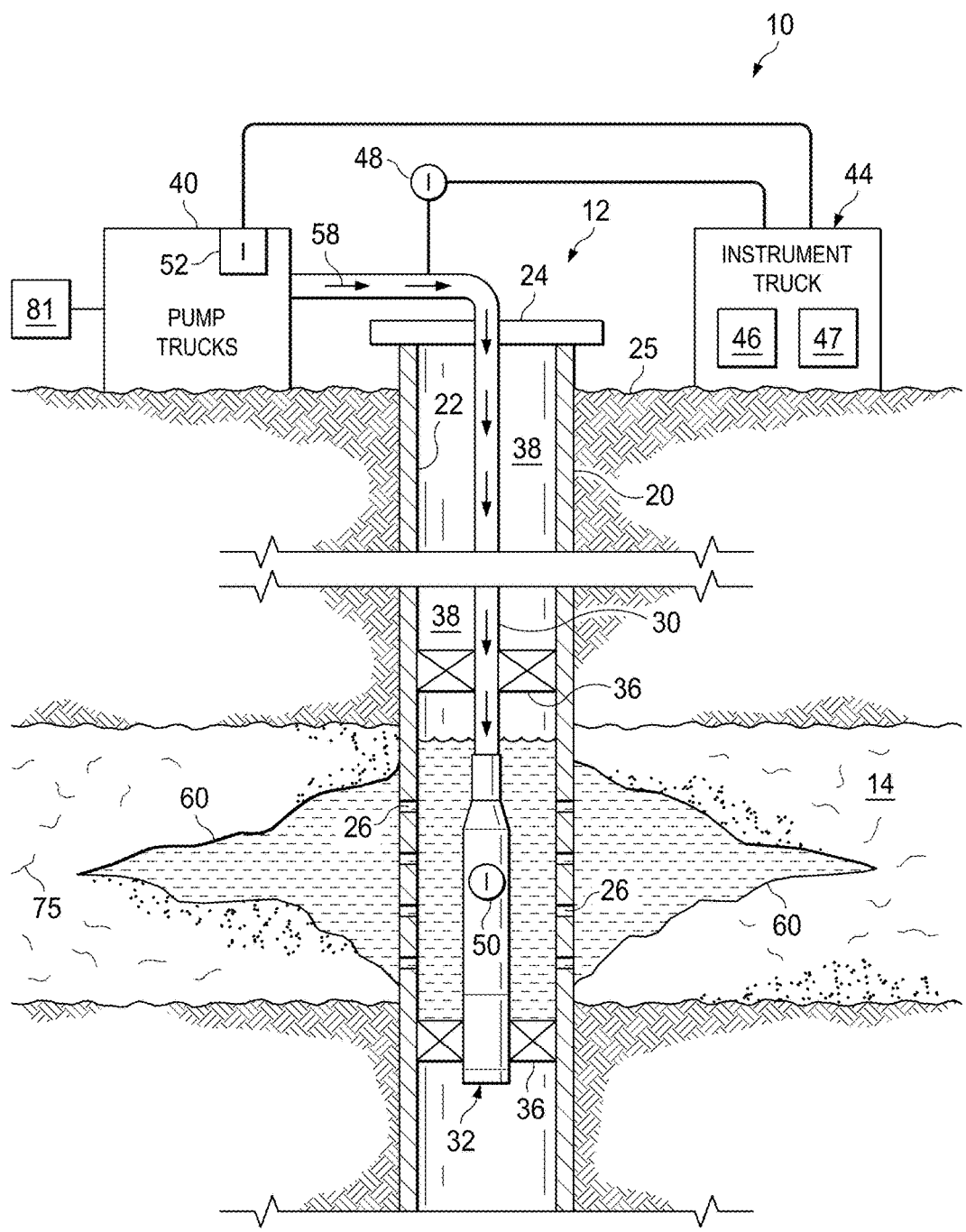
FIG. 25 shows an example of a fracture treatment for a well.

FIG. 25 illustrates an example of a fracture treatment 10 for a well 12. The well 12 can be a reservoir or formation 14, for example, an unconventional reservoir in which recovery operations in addition to conventional recovery operations are practiced to recover trapped hydrocarbons. Examples of unconventional reservoirs include tight-gas sands, gas and oil shales, coalbed methane, heavy oil and tar sands, gas-hydrate deposits, to name a few. In some implementations, the formation 14 includes an underground formation of naturally fractured rock containing hydrocarbons (for example, oil, gas or both). For example, the formation 14 can include a fractured shale. In some implementations, the well 12 can intersect other suitable types of formations 14, including reservoirs that are not naturally fractured in any significant amount.

The well 12 can include a well bore 20, casing 22 and well head 24. The well bore 20 can be a vertical or deviated bore. The casing 22 can be cemented or otherwise suitably secured in the well bore 12. Perforations 26 can be formed in the casing 22 at the level of the formation 14 to allow oil, gas, and by-products to flow into the well 12 and be produced to the surface 25. Perforations 26 can be formed using shape charges, a perforating gun or otherwise.

For the fracture treatment 10, a work string 30 can be disposed in the well bore 20. The work string 30 can be coiled tubing, sectioned pipe or other suitable tubing. A fracturing tool 32 can be coupled to an end of the work string 30. Packers 36 can seal an annulus 38 of the well bore 20 above and below the formation 14. Packers 36 can be mechanical, fluid inflatable or other suitable packers.

One or more pump trucks 40 can be coupled to the work string 30 at the surface 25. The pump trucks 40 pump fracture fluid 58 down the work string 30 to perform the fracture treatment 10 and generate the fracture 60. The fracture fluid 58 can include a fluid pad, proppants and/or a flush fluid. The pump trucks 40 can include mobile vehicles, equipment such as skids or other suitable structures. The fracturing fluid can be a cross-linked gel, linear gel, synthetic polymer gel, or slickwater with friction reducer. The fluid can be proppant-laden.

One or more instrument trucks 44 can also be provided at the surface 25. The instrument truck 44 can include a fracture control system 46 and a fracture simulator 47. The fracture control system 46 monitors and controls the fracture treatment 10. The fracture control system 46 can control the pump trucks 40 and fluid valves to stop and start the fracture treatment 10 as well as to stop and start the pad phase, proppant phase and/or flush phase of the fracture treatment 10. The fracture control system 46 communicates with surface and/or subsurface instruments to monitor and control the fracture treatment 10. In some implementations, the surface and subsurface instruments may comprise surface sensors 48, down-hole sensors 50 and pump controls 52.

A quantity of energy applied by the fracture control system 46 to generate the fractures 60 in the reservoir or formation 14 can be affected not only by the properties of the reservoir rock in the formation but also by the organic matter (for example, kerogen 75) intertwined within the rock matrix.

Figure 30:
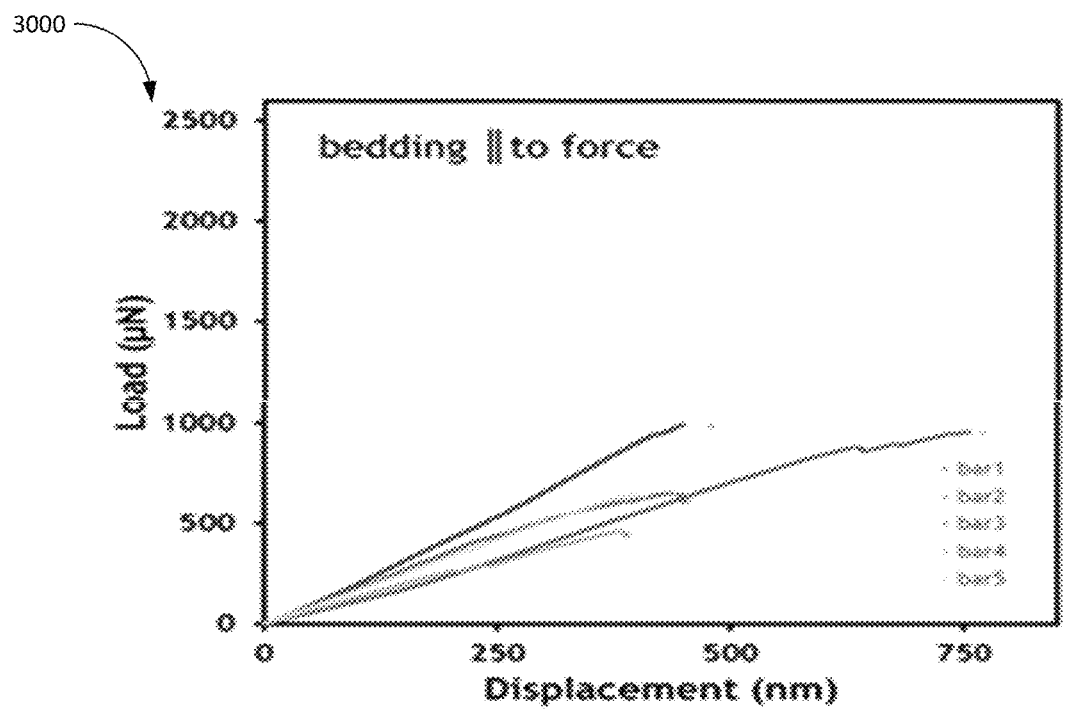
FIG. 30 is a plot showing load versus displacement curves on multiple rock sample beams.
Figure 31:
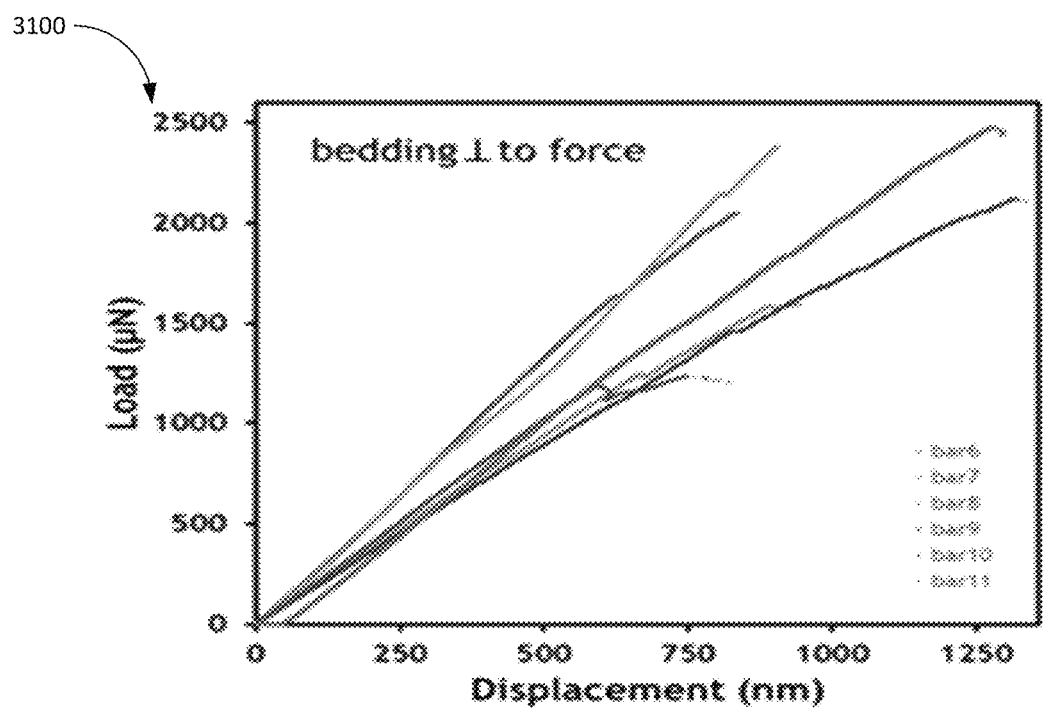
FIG. 31 is a plot showing load versus displacement curves on multiple rock sample beams.

In one example, five micro-scale cantilever rock sample beams were prepared, each with a longitudinal axis parallel to the bedding plane as shown in FIG. 26A. Six micro-scale cantilever beams were prepared, each with a longitudinal axis perpendicular to the bedding plane as shown in FIG. 26A. The nano-indenter tip force was applied perpendicular to the longitudinal axis. FIG. 30 is a plot 3000 showing load versus displacement curves of the six micro-scale rock sample beams prepared with longitudinal axes parallel to the bedding planes. FIG. 31 is a plot 3100 showing load versus displacement curves of the five micro-scale rock sample beams prepared with longitudinal axes perpendicular to the bedding planes. The load versus displacement curves reveal that more energy was required to fail the beams of the plot 3000 than those of the plot 3100. Using the classical beam theory (Bernoulli's beam or Euler's beam), the Young's Modulus E was determined using load and displacement values from the linear elastic portion of the cantilever beam loading curves shown in plots 3000 and 3100.

TABLE 4

Beam dimensions and mechanical properties

| Test | dL (µm) | $L_b$ (µm) | b (µm) | h (µm) | I (µm$^4$) | P (µN) | w (µm) | E (GPa) |
|---|---|---|---|---|---|---|---|---|
| 1 | 25.66 | 23.71 | 9.21 | 9.21 | 599.6 | 423.4 | 200.1 | 17.6 |
| 2 | 25.64 | 23.72 | 8.83 | 8.63 | 472.9 | 240.6 | 200.0 | 12.7 |
| 3 | 24.78 | 22.12 | 8.51 | 9.41 | 590.9 | 359.9 | 200.0 | 13.0 |
| 4 | 17.79 | 16.69 | 6.53 | 6.94 | 181.9 | 258.8 | 200.2 | 12.1 |
| 5 | 27.59 | 26.14 | 9.04 | 9.10 | 567.7 | 337.5 | 200.2 | 19.2 |
| 6 | 29.31 | 28.47 | 8.45 | 8.91 | 498.1 | 775.2 | 300.5 | 41.6 |
| 7 | 18.56 | 17.75 | 8.01 | 7.12 | 240.9 | 765.5 | 300.2 | 21.1 |
| 8 | 28.75 | 26.17 | 9.77 | 8.16 | 442.4 | 573.4 | 300.0 | 29.6 |
| 9 | 29.26 | 28.76 | 8.84 | 9.45 | 621.7 | 540.2 | 300.3 | 23.5 |
| 10 | 28.79 | 27.63 | 9.44 | 8.98 | 569.7 | 612.5 | 300.4 | 26.8 |
| 11 | 30.87 | 29.78 | 9.21 | 9.32 | 621.3 | 547.1 | 300.0 | 27.3 |

In Table 4, which shows beam dimensions and mechanical properties, dL is the beam length, $L_b$ is the bending length, b is the beam width, h is the beam height, I is the moment of inertia, and finally P and w are load and displacement values taken from a point on the linear elastic loading portion of the load-displacement curve. The Young's modulus E was calculated from these values, where E1 is from the orientation represented by beams 1-5 and E3 is represented by the orientation in beams E6-11. E1 and E3 can be selected, which is why there is a range from 1.3 to 3. The results indicate notable anisotropy in the amount of energy required to fail the beam depending on the direction of orientation of the bedding planes relative to the direction of load. The degree of anisotropy is expected to vary from one shale to the next. The energies obtained can be used in modeling predictions of hydraulic fracturing in shale.

Figure 27:
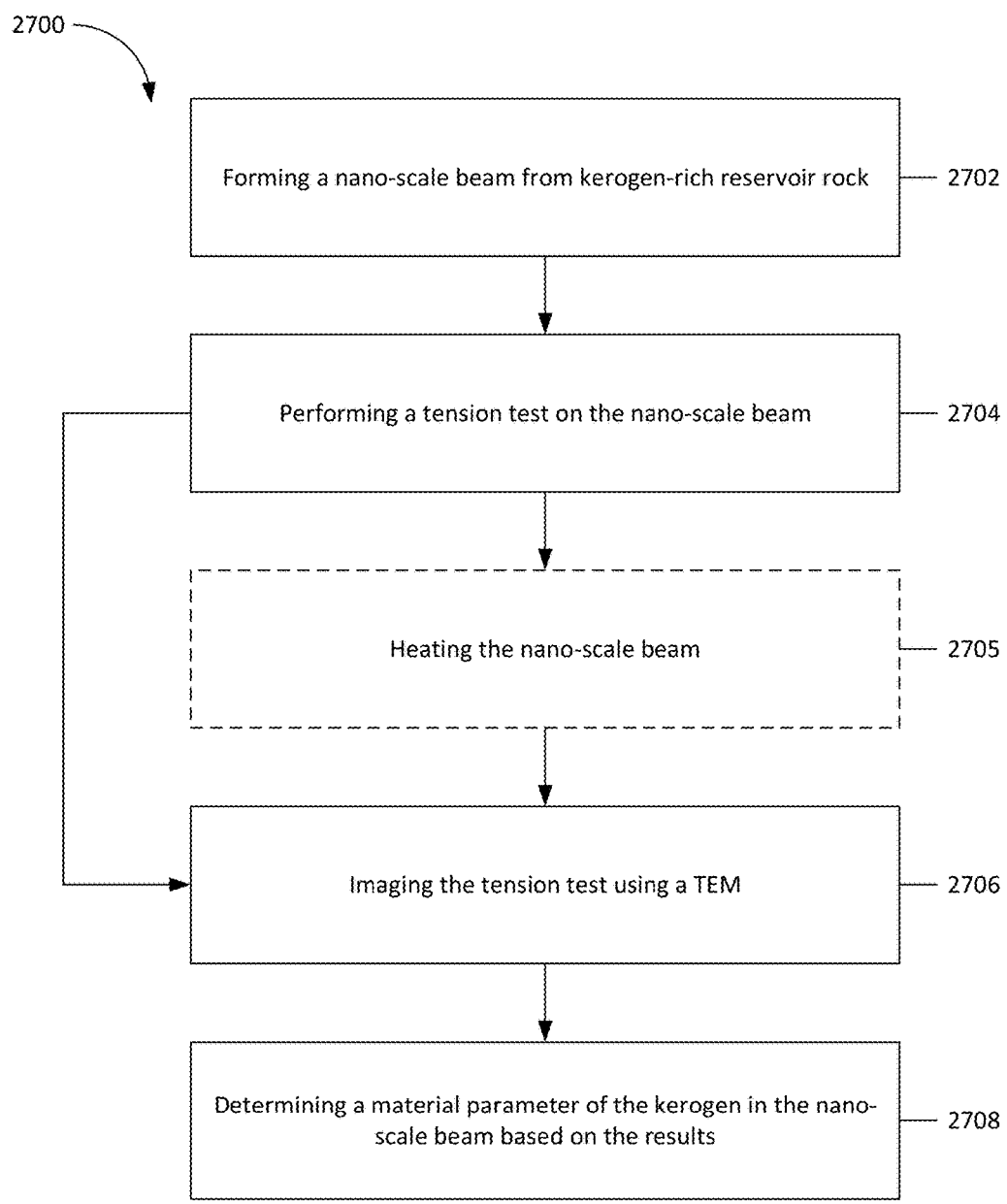
FIG. 27 is a flowchart that shows an example process for determining properties of a nano-scale rock sample.

FIG. 27 is a flowchart that shows an example process 2700 for determining properties of a nano-scale rock sample. At 2702, a nano-scale beam is cut and formed from a kerogen-rich retrieved reservoir rock. The nano-scale beam has a minimum dimension of at least 100 nanometers (nm) and a maximum dimension of at most 1000 nm. For example, the cross-sectional dimension can be of the order of hundred nanometers. For TEM imaging, a minimum dimension of less than 100 nm is also possible. In some implementations, nano-scale beams of the same or different cross-sectional dimensions can be manufactured using a FIB described earlier. Analyzing a composite material at a nano-scale level can enable identifying the representative elementary volume (REV) of the material. In granular composite materials, for example, shale, cement, or similar granular composite materials, the REV is an intrinsic length scale at and above which the material behaves mechanically as the bulk material, and below which the material starts to behave as individual granular components. The material behavior below the intrinsic length scale can depend upon the specific grains being analyzed.

At 2704, a tension test is performed on the nano-scale beam. For example, the tension test can be a cantilever test in which the nano-scale beam is loaded using a nano-indenter such as those described earlier. At 2706, the tension test is imaged using a TEM. For example, the nano-scale beam and the nano-indenter can be positioned inside the TEM and TEM images can be captured while the tension test is in progress. Because a TEM operates in transmission mode, it is possible to see near atomic scale features. For example, in crystalline materials, features known as dislocations can possibly be identified and observed during deformation and failure. During the in situ TEM beam testing of shale, movement of dark features in certain grains during the imaging suggest that dislocations may be moving or nucleating (or both). The TEM can also be used to perform selected area diffraction (SAD) where a diffraction pattern of crystalline regions can be captured and analyzed to determine the crystallographic orientation of grains. This orientation is well known to influence the values of the various mechanical properties, such as Young's modulus or the shear modules.

In some implementations, as an option, at 2705, the nano-scale beam can be heated to study the effect of heat on the mechanical properties of the nano-scale beam. For example, heat can be applied to the nano-indenter tip or to the stage on which the nano-scale beam is positioned or both. In some implementations, the tension test and the imaging can be performed without the application of heat to further study the effect of heat on the mechanical properties of the nano-scale beam. A Hysitron Pi-85 Pico-indenter was used to load the nano-micro-beams under displacement control mode, at a rate of between 1 nm/s and 100 nm/s, for example, between 5 nm/s and 20 nm/s, for example, 10 nm/s. The indenter tip was placed at the end of the beam, centered along the y-axis. The indenter tip is a flat circular punch geometry, with a diameter of 5 µm or other, different geometry or diameter. All loading experiments were performed in situ under the TEM, where loading of the nano-scale beams continued until failure. For a material with REV in the micro- or hundreds of nano-scale range (for example, source shale), TEM in situ mechanical testing offers a way to probe the individual composite material behavior at the REV level and even down further, allowing us to understand the material's behavior and response.

Figure 28:
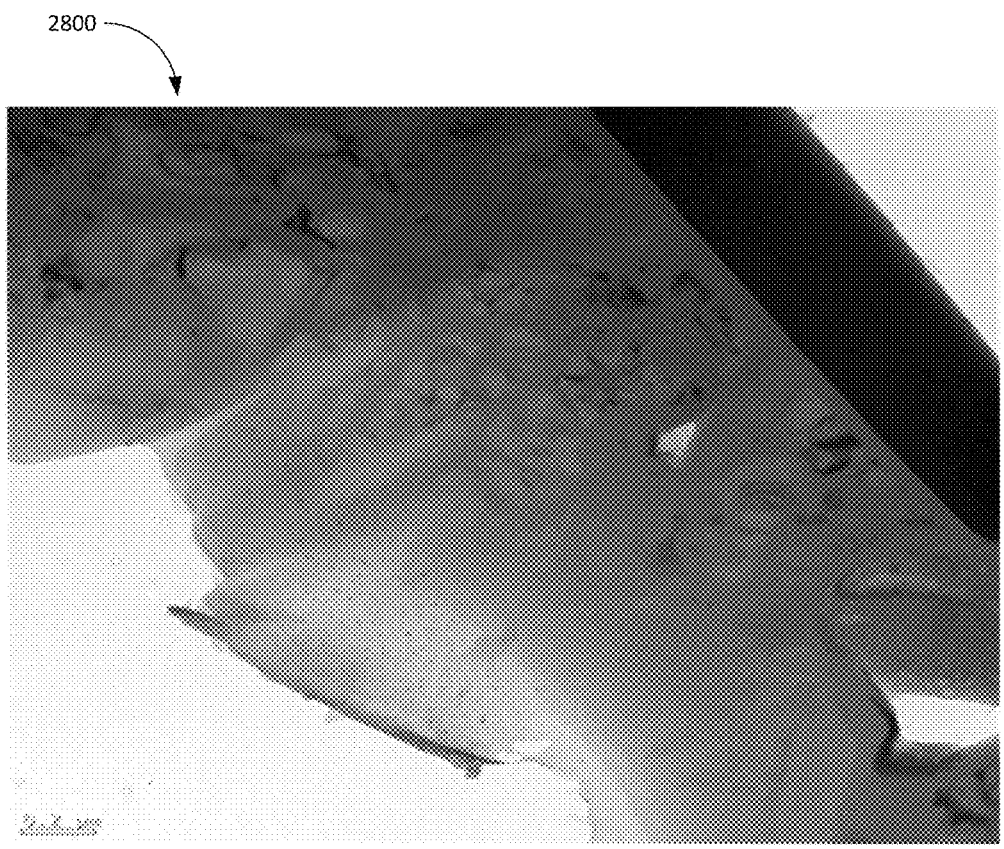
FIG. 28 is a Transmission Electron Microscope (TEM) image 2800 of a nano-scale beam prior to failure.
Figure 29:
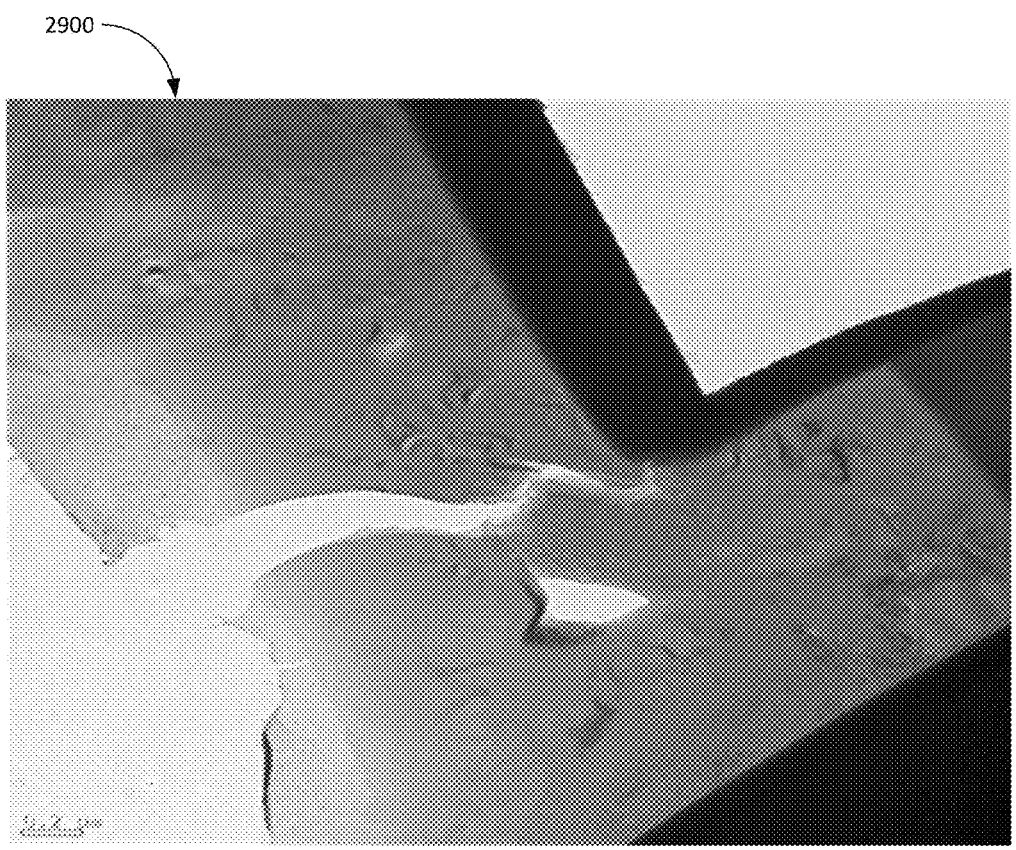
FIG. 29 is a TEM image 2900 of a nano-scale beam after failure.

FIG. 28 is a Transmission Electron Microscope (TEM) image 2800 of a nano-scale beam prior to failure. FIG. 29 is a TEM image 2900 of a nano-scale beam after failure. The post-failure image 2900 shows a tortuous crack across the beam support together with a conchoidal or even tortuous fracture tip propagation, which indicates an initiation of a fracture in a composite organic matter intertwined with minerals. Such fracture propagations have no continual preference or alignment of weakening planes.

At 2708, a material parameter of the nano-micro-scale beam is determined based on results of the tension test and images obtained.

Figure 32:
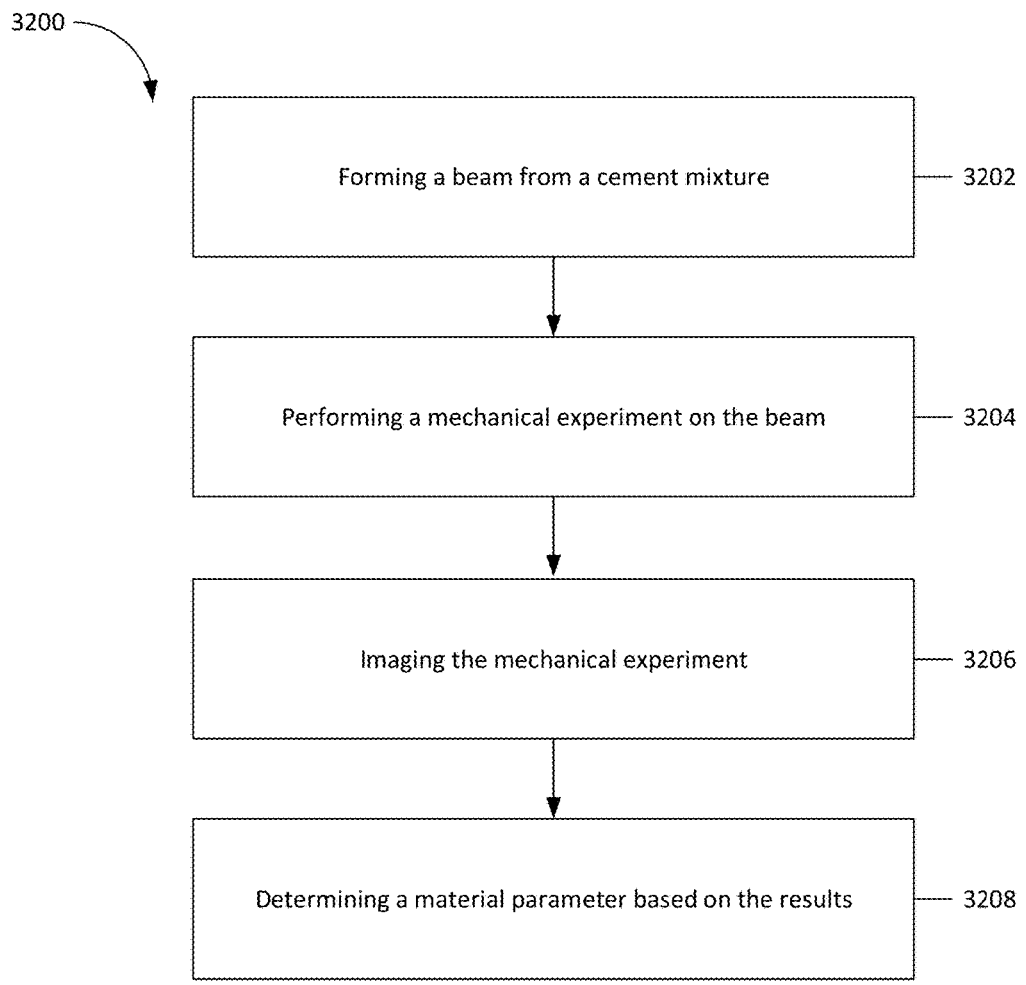
FIG. 32 is a flowchart that shows an example process for determining properties of a cement mixture.

The techniques described in this disclosure can be implemented using a cement mixture, for example, a mixture of cement and an organic additive such as polymers or fibers. In other words, micro- and nano-scale beams can be prepared and tested using nano-indentation experiments implemented in a SEM or TEM. FIG. 32 is a flowchart 3200 that shows an example process for determining properties of a cement mixture. At 3202, a beam can be formed from a cement mixture. The cement mixture can include cement and an additive, for example, an organic additive such as polymer or fibers. A maximum dimension of the beam can be at most 1000 µm. In some implementations, the beam can be a nano-scale beam with a maximum dimension of at most 1000 nm. At 3204, a mechanical experiment can be performed on the beam. The mechanical experiment can be a tension test (for example, a cantilever test) or a compression test. At 3206, the mechanical experiment can be imaged, for example, using a SEM or TEM. That is, the beam can be positioned inside the SEM or TEM and can be imaged while the mechanical experiment is being performed. At 3208, a material parameter of the additive in the beam can be determined based on results of the mechanical experiment and the images. In some implementations, before forming the beam, the cement mixture can be treated with an additive, for example, an organic additive. An effect of the additive on the mechanical properties, for example, of the cement mixture, of the cement, or of the additive, can be determined based on the results of the mechanical experiment and the images. The results can be used to develop cement mixtures for specific cementing applications. For example, cement mixtures developed using the results of the mechanical experiment and the images can be used in wellbore applications, for example, to case all or portions of a wellbore.

Thus, particular implementations of the subject matter have been described. Other implementations are within the scope of the following claims.

The invention claimed is:

1. A method comprising:
    forming a beam from a cement mixture comprising cement and a polymer, wherein a maximum dimension of the beam is at most 1000 micrometer (µm);
    performing a mechanical experiment on the beam, wherein the mechanical experiment comprises a tension test or a compression test;
    imaging the mechanical experiment using a scanning electron microscope (SEM) or a transmission electron microscope (TEM); and
    determining a material parameter of the polymer in the beam based on results of the mechanical experiment and images obtained responsive to the imaging;
    before forming the beam, treating the cement mixture with an organic additive configured to alter properties of the polymer in the cement mixture; and
    determining an effect of organic additive on the polymer in the mixture based on the material parameter of the polymer in the beam.

2. The method of claim 1, wherein the mechanical experiment is the tension test, and wherein the material parameter of the polymer in the beam comprises a tensile strength of the beam.

3. The method of claim 1, wherein the tension test is a cantilever test, wherein performing the cantilever test comprises applying a force of the order of micro-Newtons on a free-end of the beam, wherein determining the material parameter comprises measuring a bending of the cantilever responsive to force.

4. The method of claim 1, wherein the maximum dimension of the beam is at least 100 nanometer (nm) and at most 1000 nm.

5. The method of claim 1, wherein the beam is formed using a focused ion beam.

* * * * *